US008680094B2

(12) United States Patent
D'Mello et al.

(10) Patent No.: US 8,680,094 B2
(45) Date of Patent: Mar. 25, 2014

(54) 1, 4-BENZOXAZINE COMPOUNDS AND DERIVATIVES THEREOF AS THERAPEUTIC DRUGS FOR THE TREATMENT OF NEURODEGENERATIVE CONDITIONS

(75) Inventors: Santosh R. D'Mello, Dallas, TX (US);
Edward R. Biehl, Dallas, TX (US);
Haribabu Ankati, Dallas, TX (US);
Shashidhar Kumar Akubathini,
Karimnagar (IN)

(73) Assignees: Board of Regents, The University of Texas System, Austin, TX (US);
Southern Methodist University, Dallas, TX (US)

( * ) Notice: Subject to any disclaimer, the term of this patent is extended or adjusted under 35 U.S.C. 154(b) by 208 days.

(21) Appl. No.: 13/059,035

(22) PCT Filed: Aug. 14, 2009

(86) PCT No.: PCT/US2009/053932
§ 371 (c)(1),
(2), (4) Date: Jul. 8, 2011

(87) PCT Pub. No.: WO2010/019911
PCT Pub. Date: Feb. 18, 2010

(65) Prior Publication Data
US 2012/0094991 A1 Apr. 19, 2012

Related U.S. Application Data

(60) Provisional application No. 61/089,443, filed on Aug. 15, 2008, provisional application No. 61/177,866, filed on May 13, 2009.

(51) Int. Cl.
*C07D 241/40* (2006.01)
*A61K 31/535* (2006.01)
(52) U.S. Cl.
USPC ........................................ 514/230.5; 544/105
(58) Field of Classification Search
USPC ........................................ 544/105; 514/230.5
See application file for complete search history.

(56) References Cited

FOREIGN PATENT DOCUMENTS

FR 2248843 A1 5/1975

OTHER PUBLICATIONS

Sastry et al. Indian Journal of Chemistry, Section B: Organic Chemistry Including Medicinal Chemistry (1987), 26B(7), 662-5.*
Ilas, et al., "Novel potent and selective thrombin inhibitors based on a central 1,4-bensoxazin-3(4H)-one scaffold", Journal of Medical Chemistry, (2008) 51:9, pp. 2863-2867.
Reddy, S., et al., "Synthesis & Biologivcal Activity of Some Nes 6-Isothiocyanato-,6-N- not N, N-Bis(Methoxycarbonyl) Guanidino 3/4-&6-(2-Aryl/2-Arylaminothiazol-4Yl)-2H-1,4-Benzoxazin-3(4H)-Ones", Indian Journal of Chemistry:IJC, Council of Scientific and Industrial Research, IN, (1987), 26B:7, pp. 662-665.
Gezginci, H., et al., "Synthesis of New 2-Arylidene-2H-1, 4-Benzoxazin-3(4H)-Ones", Farmaco, Societa Chimica Italiana, Pavia, IT, (1997), 52:4, pp. 255-256.
Balderamos, Michael, et al., "Synthesis and Structure-Activity Relationship Studies of 3-Substituted Indolin-2-ones as Effective Neuroprotective Agents," Experimental Biology and Medicine, (2008), 233:1395-1402.
Bhave, Sanjiv V., et al., "Phosphatidylinositol 3'-OH Kinase and Protein Kinase A Pathways Mediate the Anti-Apoptotic Effect of Pituitary Adenlyly Cyclase-Activating Polypeptide in Cultured Cerebellar Granule Neurons: Modulation by Ethanol," Journal of Neurochemistry, (2004), 88:359-369.
Brand, Andrea H., et al., "Targeted Gene Expression as a Means of Altering Cell Fates and Generating Dominant Phenotypes," Development, (1993), 118:401-415.
Chen, Hsin-Mei, et al., "Inhibition of ATF-3 Expression by B-Raf Mediates the Neuroprotective Action of GW5074," Journal of Neurochemistry, (2008), 105:1300-1312.
Chen, Hsin-Mei, et al., "A Chemical Compound Commonly Used to Inhibit PKR, {8-(imidazol-4-ylmethylene)-6H-Azolidino[5,4-g] Benzothiazol-7-one}, Protects Neurons by Inhibiting Cyclin-Dependent Kinase," European Journal of Neuroscience, (2008), vol. 28, pp. 2003-2016.
Chin, Paul C., et al., "The C-Raf Inhibitor GW5074 Provides Neuroprotection in Vitro and in an Animal Model of Neurodegeneration through a MEK-ERK and Akt-Independent mechanism," Journal of Neurochemistry, (2004), 90:595-608.
D'Mello, Santosh, et al., "Induction of Apoptosis in Cerebellar Granule Neurons by Low Potassium: Inhibition of Death by Insulin-Like Growth Factor I and cAMP," Proc. Natl. Acad. Sci., Dec. 1993, vol. 90, pp. 10989-10993.
D'Mello, Santosh, et al., "Treating Neurodegenerative Conditions through the Understanding of Neuronal Apoptosis," Current Drug Targets—CNS & Neurological Disorders, (2005), 4:3-23.
Estus, Steven, et al., "Altered Gene Expression in Neurons During Programmed Cell Death: Identification of C-Jun as Necessary for Neuronal Apoptosis," The Journal of Cell Biology, (1994), vol. 127, pp. 1717-1727.
Fossgreen, Anke, et al., "Transgenic *Drosophila* Expressing Human Amyloid Precursor Protein Show 7-Secretase Activity and a Blistered-Wing Phenotype," Proc. Natl. Acad. Sci., Nov. 1998, vol. 95, pp. 13703-13708.
Greeve, Isabell, et al., Age-Dependent Neurodegeneration and Alzheimer-Amyloid Plaque Formation in Transgenic *Drosophila*, The Journal of Neuroscience, Apr. 21, 2004, 24 (16):3899-3906.
Hai, Tsonwin, et al., "ATF3 and Stress Responses," Gene Expression, (1999), vol. 7, pp. 321-335.
Ham, Jonathan, et al., "A C-Jun Dominant Negative Mutant Protects Sympathetic Neurons Against Programmed Cell Death," Neuron, May 1995, vol. 14, pp. 927-939.
Hanson, Jr., Martin G., et al., "Cyclic AMP Elevation is Sufficient to Promote the Survival of Spinal Motor Neurons in Vitro," The Journal of Neuroscience, Sep. 15, 1998, 18(18):7361-7371.

(Continued)

*Primary Examiner* — Kahsay Habte
(74) *Attorney, Agent, or Firm* — Chainey P. Singleton; Edwin S. Flores; Chalker Flores, LLP

(57) ABSTRACT

The present invention includes compositions and methods for inhibiting kinase activity to protect against neurodegeneration including diseases such as Alzheimer's disease, Parkinson's disease, or Huntington's disease, and conditions such as ischemic stroke comprising the step of providing the subject with a therapeutically affective amount of 1,4-benzoxazine compounds and derivatives thereof.

19 Claims, 9 Drawing Sheets

(56) References Cited

OTHER PUBLICATIONS

Hetman, Michal, et al., "Survival Signaling Pathways Activated by NMDS Receptors," Curr Top Med Chem, (2006), 6 (8):787-799.

Honda, Takahiro, et al., "Synthesis of Novel 1,4-Benzoxazin-3-One Derivatives as Inhibitors Against Tyrosine Kinases," Bioorganix &Medicinal Chemistry, (2009), 17:699-708.

Johnson, Kyle, et al., "Inhibition of Neuronal Apoptosis by the Cyclin-Dependent Kinase Inhibitor GW8510: Identification of 3' Substituted Indolones as a scaffold for the Development of Neuroprotective Drugs," Journal of Neurochemistry, (2005), 93:538-548.

Li, Mingtao, et al., "Cyclic AMP Promotes Neuronal Survival by Phosphorylation of Glycogen Synthase Kinase 3B," Molecular and Cellular Biology, Dec. 2000, pp. 9356-9363.

Linseman, Daniel A., et al., "Inactivation of the Myocyte Enhancer Factor-2 Repressor Histone Deacetylase-5 by Endogenous Ca2+/Calmodulin-Dependent Kinase II Promoted Depolarization-Mediated Cerebellar Granule Neuron Survival," The Journal of Biological Chemistry, Oct. 17, 2003, vol. 278, No. 42, pp. 41472-41481.

Majdzadeh, Nazanin, et al., "HDAC4 Inhibits Cell Cycle Progression and Protects Neurons from Cell Death," Dev. Neurobiol., Jul. 2008, 68(8):1076-1092.

Morozova, Nadya, et al., "Glutathione Depletion in Hippocampal Cells Increases Levels of H and L Ferritin and Glutathione S-Transferase mRNAs," Genes to Cells, (2007), 12:561-567.

Morrison, Brad E., et al., "Neuroprotection by Histone Deacetylase-Related Protein," Molecular and Cellular Biology, May 2006, pp. 3550-3564.

Murphy, Timothy H., et al., "Immature Cortical Neurons are uniquely sensitive to Glutamate Toxicity by Inhibition of Cystine Uptake," FASEB, (1990), 4:1624-1633.

Ratan, Rajiv R., et al., "Macromoleculat Synthesis Inhibitors Prevent Oxidative Stress-Induced Apoptosis in Embryonic Cortical Neurons by Shunting Cysteine from Protein Synthesis to Glutathione," The Journal of Neuroscience, Jul. 1994, 14 (7):4385-4392.

Rydel, Russell, E., et al., cAMP Analogs Promote Survival and Neurite Outgrowth in Cultures of Rat Sympathetic and Sensory Neurons Independently of Nerve Growth Factor., Proc. Natl. Acad. Sci., Feb. 1988, vol. 85, pp. 1257-1261.

See, Violaine, et al., "Calcium-Calmodulin-Dependent Protein Kinase Type IV (CaMKIV) Ibhibits Apoptosis Induced by Potassium Deprivation in Cerebellar Granule Neurons,".

Watson, Andrea, et al., "Phophorylation of c-Jun is Necessary Apoptosis Induced by Survival Signal Withdrawal in Cerebellar Granule Neurons," The Journal of Neuroscience, Jan. 15, 1998, 18(2):751-762.

Yalcin, Asligul, et al., "Apoptosis in Cerebellar Granule Neurons is associated with Reduced Interaction Between CRAB-Binding Protein and NF-KB," Journal of Neurochemistry, (2003), 84:397-408.

Extended European Search Report for Application No. 09807384, dated Jul. 12, 2011, 8 pages.

* cited by examiner $p < 0.05$

1, 4-BENZOXAZINE COMPOUNDS AND DERIVATIVES THEREOF AS THERAPEUTIC DRUGS FOR THE TREATMENT OF NEURODEGENERATIVE CONDITIONS

CROSS-REFERENCE TO RELATED APPLICATIONS

This Non-Provisional Patent Application claims is a 371 application of PCT/US2009/053932 files Aug. 14, 2009 and claims priority to U.S. Provisional Patent Application Ser. No. 61/089,443, filed Aug. 15, 2008 and U.S. Provisional Patent Application Ser. No. 61/177,866 filed May 13, 2009 the contents of which are all incorporated by reference herein in their entirety.

STATEMENT OF FEDERALLY FUNDED RESEARCH

This invention was made with government support under Contract No. 1R01 NS047201 awarded by the NIH and Contract No. HR001 1-06-0032 awarded by DOD-DARPA. The government has certain rights in this invention.

TECHNICAL FIELD OF THE INVENTION

The present invention relates in general to the field of neurodegenerative disorders, and more particularly, to novel compositions and methods to protect against neurodegeneration including diseases such as Alzheimer's disease, Parkinson's disease, Amyotropic lateral sclerosis (ALS), or Huntington's disease, and conditions such as ischemic stroke and traumatic brain injury.

BACKGROUND ART

Without limiting the scope of the invention, its background is described in connection with novel therapeutic compounds that act as neuroprotective agents against neurodegenerative pathologies including Alzheimer's disease, Parkinson's disease, or Huntington's disease, and conditions such as ischemic stroke.

Diseases such as Alzheimer's disease, Parkinson's disease, ALS, Huntington's disease, and conditions such as ischemic stroke and traumatic brain injury, affect millions of individuals annually and exert an enormous financial burden on society. A hallmark of these conditions is the abnormal and excessive loss of neurons. There are currently no effective strategies to prevent the neuronal death in these pathologies.

Neurodegenerative disorders, such as Alzheimer's disease (AD), is characterized by neurofibrillary tangles, neuritic plaques, and neuronal cell death. Alzheimer's is a degenerative and terminal disease for which there is no known cure and is characterized by plaques and tangles in the brain. In its most common form, it afflicts individuals over 65 years old, although a less prevalent early-onset form also exists.

DISCLOSURE OF THE INVENTION

The present inventors have synthesized and screened small-molecule chemical compounds for the ability to prevent neuronal death using a tissue culture paradigm of neurodegeneration. These investigations have led to the identification of 2-benzylidene-2H-1,4-benzoxazin-3-(4H)-one as a compound with potent neuroprotective activity. It is demonstrated herein that 2-benzylidene-2H-1,4-benzoxazin-3-(4H)-one and derivatives thereof are able to protect the susceptible neuronal populations in the brain, and hence represent a therapeutic approach to treat neurodegenerative conditions. There is currently no effective strategy to cure, mitigate or treat neurodegenerative diseases. Compounds of the 1,4-benzoxazin-3-(4H)-one class have not previously been shown to protect against neurodegeneration. These compounds represent a novel therapeutic tool.

The present invention includes 1,4-benzoxazine compounds, such as HSB13 and derivatives of it, as a novel therapeutic tool in the treatment of neurodegenerative diseases, including but not restricted to, Alzheimer's disease, Parkinson's disease, Huntington's disease, and Amyotropic lateral sclerosis, as well as neurological conditions such as ischemic stroke and traumatic brain injury. The present invention includes compositions and methods for making and using compositions that include a number of different 1,4-benzoxazine compounds and derivatives thereof. 1,4-benzoxazine compounds and derivatives thereof were evaluated in a tissue culture model of neurodegeneration. These compounds are protective in a different tissue culture model of neurodegeneration.

The present invention describes several compounds of the 1,4-benzoxazine class that are highly neuroprotective in tissue culture models of neurodegeneration. By way of hypothesis and in no way a limitation of the present invention it was found that using pharmacological inhibitors it is proposed that the mechanism of action of these compounds does not involve the Raf-MEK-ERK or PI 3 kinase-Akt signaling pathways nor other survival promoting molecules such as protein kinase A (PKA), calcium calmodulin kinase A (CaMK) and histone deacetylases (HDACs).

The 1,4-benzoxazine compounds and derivatives thereof were found to reduce striatal degeneration and improve behavioral performance in a chemically-induced mouse model of Huntington's disease. Several 1,4-benzoxazines, including compounds such as HSB-13, HSB-22, and ASK-2, protected cultured cerebellar granule neurons from death induced by low potassium treatment. HSB-13 protected HT-22 neuroblastoma cells from homocysteic-acid (HCA) induced neurotoxicity. It was also found that ASK-2 protects primary cortical neurons from HCA-induced neurotoxicity. HSB-13 reduced striatal degeneration and improves behavioral performance in the 3-nitropropionic acid mouse model of Huntington's disease.

The present invention describes studies on one of these compounds, (Z)-6-amino-2-(3,'5'-dibromo-4'-hydrozybenzylidene)-2H-benzo[b][1,4]oxazin-3(4H)-one, designated as HSB-13, in the 3-nitropropionic acid (3-NP)-induced mouse model of Huntington's disease. HSB-13 reduced striatal degeneration and improved behavioral performance in mice administered with 3-NP. The inventors found that the compound HSB-13 was protective in a well-characterized and accepted model system of Huntington's disease and a *Drosophila* model of amyloid precursor protein (APP) toxicity. The HSB-13 family of compounds and newly created derivatives thereof of the present invention represent a novel therapeutic tool in the treatment of neurodegenerative diseases.

The present invention includes 1,4-benzoxazine compounds, such as HSB13 and derivatives of it, as a novel therapeutic tool in the treatment of neurodegenerative diseases, including but not restricted to, Alzheimer's disease, Parkinson's disease, Huntington's disease, and Amyotropic lateral sclerosis, as well as neurological conditions such as ischemic stroke and traumatic brain injury. The compounds described in the present invention provide neuroprotection in a subject, e.g., a human, a nonhuman primate, a rat, a mouse, and a fly. The present invention includes compositions and methods for making and using compositions that include a number of different 1,4-benzoxazine compounds and derivatives thereof. 1,4-benzoxazine compounds and derivatives thereof were evaluated in a tissue culture model of neurodegeneration. Surprisingly, it was found that these compounds are protective in different tissue culture models of neurodegeneration.

The compounds of the present invention provide modulation of the neurological condition by modulating death, abnormal or excessive loss of one or more neurons in the subject, affecting neurotoxicity, locomotor performance in the subject, and/or the toxic effects of the amyloid precursor protein and other moieties.

The 1,4-benzoxazine compounds and derivatives thereof were found to reduce striatal degeneration and improve behavioral performance in a chemically-induced mouse model of Huntington's disease. Several 1,4-benzoxazines, including compounds such as HSB-13, HSB-22, and ASK-2, protected cultured cerebellar granule neurons from death induced by low potassium treatment. HSB-13 protected HT-22 neuroblastoma cells from homocysteic-acid (HCA) induced neurotoxicity. It also protects cortical neurons from beta-amyloid (Aβ)—induced neuronal death, a well-characterized and commonly used tissue culture model of Alzheimer's disease. ASK-2 protects primary cortical neurons from HCA-induced neurotoxicity. HSB-13 reduced striatal degeneration and improved behavioral performance in the 3-nitropropionic acid mouse model of Huntington's disease.

The present invention includes a compound of the formula:

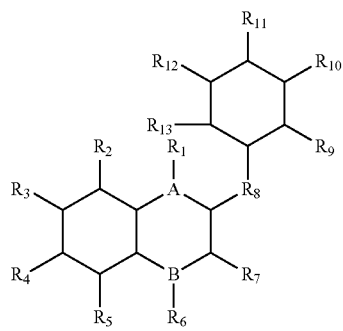

wherein A and B are selected from C, N, S, O. $R_1$-$R_7$ are independently selected from a H, a $C_1$-$C_6$ Alkyl group, a $C_1$-$C_6$ Alkenyl group, a halo group, a substituted $C_1$-$C_6$ alkyl group, a substituted $C_1$-$C_6$ alkenyl group, a carbonyl group, a carbonate ester group, an $C_1$-$C_6$ ether group, an $C_1$-$C_6$ ester group, an $C_1$-$C_6$ alkyl alkanoate group, an $C_1$-$C_6$ alkoxy group, a keto group, and an oxo group. $R_8$ is a $C_1$-$C_6$ Alkyl group, a $C_1$-$C_6$ alkenyl group, a halo group, a substituted $C_1$-$C_6$ alkyl group, a substituted $C_1$-$C_6$ alkenyl group, a carbonyl group, a carbonate ester group, an ether group, an ester group, an alkyl alkanoate group, an alkoxy group, a keto group, and an oxo group. $R_9$-$R_{13}$ are independently selected from a H, a $C_1$-$C_6$ Alkyl; a $C_1$-$C_6$ Alkenyl, a halo, a substituted $C_1$-$C_6$ alkyl, a substituted $C_1$-$C_6$ alkenyl, a carbonyl, a carbonate ester, an acetoxy group, a an acetyl group, an ether, an ester, an alkyl alkanoate group, an alkoxy group, a keto group, and an oxo group.

The present invention also provides a method of protection against, treating, reducing or modulating a neurological condition in a subject by identifying a subject in need for modulation of the neurological condition; and providing the subject with a composition. The composition has the structure:

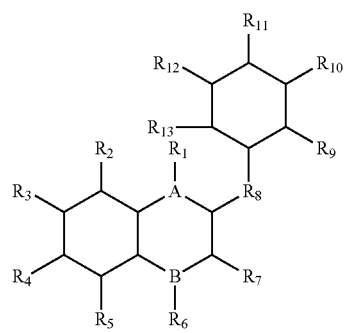

wherein A is selected from C, N, S, O; B is selected from C, N, S, O; R1-R7 are independently selected from a H, a $C_1$-$C_6$ Alkyl group, a $C_1$-$C_6$ Alkenyl group, a halo group, a substituted C1-C6 alkyl group, a substituted C1-C6 alkenyl group, a carbonyl group, a carbonate ester group, an C1-C6 ether group, an C1-C6 ester group, an C1-C6 alkyl alkanoate group, an C1-C6 alkoxy group, a keto group, and an oxo group; R8 is a C1-C6 Alkyl group, a C1-C6 alkenyl group, a halo group, a substituted C1-C6 alkyl group, a substituted C1-C6 alkenyl group, a carbonyl group, a carbonate ester group, an ether group, an ester group, an alkyl alkanoate group, an alkoxy group, a keto group, and an oxo group; and R9-R13 are independently selected from a H, a C1-C6 Alkyl; a C1-C6 Alkenyl, a halo, a substituted C1-C6 alkyl, a substituted C1-C6 alkenyl, a carbonyl, a carbonate ester, an acetoxy group, a an acetyl group, an ether, an ester, an alkyl alkanoate group, an alkoxy group, a keto group, and an oxo group.

The present invention provides a method of reducing, ameliorating, treating or protecting against a neurodegenerative condition in a subject by identifying a subject in need of protection against the neurodegenerative condition and providing the subject with a therapeutically affective amount of a composition having the formula:

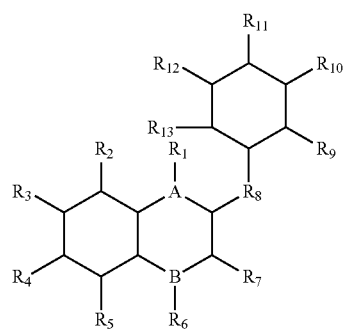

wherein A is selected from C, N, S, O; B is selected from C, N, S, O; R1-R7 are independently selected from a H, a C1-C6 Alkyl group, a C1-C6 Alkenyl group, a halo group, a substituted C1-C6 alkyl group, a substituted C1-C6 alkenyl group, a carbonyl group, a carbonate ester group, an C1-C6 ether group, an C1-C6 ester group, an C1-C6 alkyl alkanoate group, an C1-C6 alkoxy group, a keto group, and an oxo group; R8 is a C1-C6 Alkyl group, a C1-C6 alkenyl group, a halo group, a substituted C1-C6 alkyl group, a substituted C1-C6 alkenyl group, a carbonyl group, a carbonate ester group, an ether group, an ester group, an alkyl alkanoate group, an alkoxy group, a keto group, and an oxo group; and R9-R13 are independently selected from a H, a C1-C6 Alkyl;

a C1-C6 Alkenyl, a halo, a substituted C1-C6 alkyl, a substituted C1-C6 alkenyl, a carbonyl, a carbonate ester, an acetoxy group, a an acetyl group, an ether, an ester, an alkyl alkanoate group, an alkoxy group, a keto group, and an oxo group.

In another embodiment, the present invention also includes compositions and methods for inhibiting kinases in a subject comprising the steps of: identifying the subject needing protection against increased kinase activity; providing the subject with an amount of a composition effective to decrease kinase activity in the subject comprising the formula:

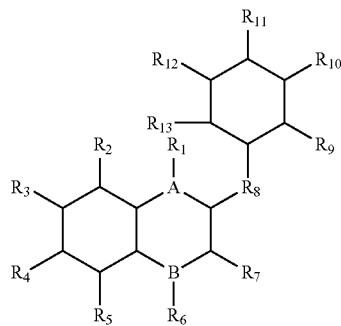

wherein, A is selected from C, N, S, O; B is selected from C, N, S, O; $R_1$-$R_7$ are independently selected from a H, a C1-C6 Alkyl group, a C1-C6 Alkenyl group, a halo group, a substituted C1-C6 alkyl group, a substituted C1-C6 alkenyl group, a carbonyl group, a carbonate ester group, an C1-C6 ether group, an C1-C6 ester group, an C1-C6 alkyl alkanoate group, an C1-C6 alkoxy group, a keto group, and an oxo group; $R_8$ is a C1-C6 Alkyl group, a C1-C6 alkenyl group, a halo group, a substituted C1-C6 alkyl group, a substituted C1-C6 alkenyl group, a carbonyl group, a carbonate ester group, an ether group, an ester group, an alkyl alkanoate group, an alkoxy group, a keto group, and an oxo group; and $R_9$-$R_{13}$ are independently selected from a H, a C1-C6 Alkyl; a C1-C6 Alkenyl, a halo, a substituted C1-C6 alkyl, a substituted C1-C6 alkenyl, a carbonyl, a carbonate ester, an acetoxy group, a an acetyl group, an ether, an ester, an alkyl alkanoate group, an alkoxy group, a keto group, and an oxo group.

In one aspect, the method further comprises the step of measuring the level of kinase activity in the subject. In another aspect, the subject needing protection against an increase in kinase activity has a neurological condition, e.g., Alzheimer's disease, Parkinson's disease, Huntington's disease, a stroke, or an ischemic stroke. In one aspect, the condition comprises a viral infection, e.g., a retroviral infection such as HIV. In another aspect, the decrease in kinase activity protects against a neurological condition comprising death of one or more neurons, loss of one or more neurons, prevention of toxicity in one or more neurons, improved locomotor performance, or protection against toxic effects of an amyloid precursor protein and other moieties. In one aspect, the subject has cancer. In yet another aspect, the kinases inhibited comprise at least one of GSK3α, GSK3β, p38β, and B-Raf. In another related aspect, the kinases inhibited comprise at least one of CDK1, CDK2, ROCK1, JNK2, MLK3, and c-Raf. The inhibitor may be provided at, e.g., between 100 and 500 nM. The method may further comprise the step of determining the activity of at least one of GSK3α, GSK3β, p38α, p38β, B-Raf, CDK1, CDK2, JNK2, JNK3, and MLK3 prior to providing the subject with the compound and then determining the activity after treatment.

Another embodiment of the present invention provides methods and compositions used to treat diseases involving deregulation of apoptosis including cancer, autoimmunodiseases, AIDS and other diseases of the immune system. Similarly, the instant invention provides methods and compositions used to treat conditions that are affected by kinases, e.g., inhibition of kinases whose activation is detrimental to neuronal survival. The present invention provides methods and compositions used to affect kinase activation of, e.g., GSK3α, GSK3β, p38β, and B-Raf.

DESCRIPTION OF THE DRAWINGS

For a more complete understanding of the features and advantages of the present invention, reference is now made to the detailed description of the invention along with the accompanying figures and in which:

FIG. 6A shows the protective effect of HSB-13 on HT-22 cells against HCA-induced toxicity. HT-22 cells were treated with no additives (Un), 1.5 mM HCA, or 1.5 mM HCA plus 25 µM HSB-13, 25

μM ASK-2a, and 25 μM HSB-22. In FIG. 6A, the appearance of the cultures at 24 h after treatment was visualized by phase-contrast microscopy (Phase). Cell death was evaluated using DAPI and TUNEL staining; FIG. 6B, shows the quantification of neuronal viability by DAPI staining. Viability was expressed as % of untreated cultures (control);

FIG. 7A is a plot that shows the protective effect of HSB-13 against 3-NP neurotoxicity in vivo: In FIG. 7A, Histological analysis. Cresyl violet staining of 40 μm coronal sections from control, 3-NP, and 3-NP+HSB-13-treated mice. Top panels: Low magnification showing selective loss of cells in the striatum; Lower panels: High magnification image of dorsolateral part of the striatum; FIG. 7B shows graphs that summarize the locomotor activity measurements of mice administered with saline (control), 3-NP and 3-NP+HSB-13. Doses and conditions of administration are detailed in Methods. Activity was measured over a 15 min period. Shown are: a) total movement time; b) total movement distance; c) average distance per movement; d) mean velocity. Bars indicate mean±SD. *Indicates statistical significance between 3-NP and 3-NP+HSB-13 values (P-value <0.05). Statistical analysis was performed using an unpaired, two-tailed Student's T test; FIG. 8 is an image showing HSB-13 protects HT-22 cells against HCA-induced toxicity. HT-22 cells were treated with no additives (Control), 2 mM HCA, or 2 mM HCA+25 μM HSB-13. The appearance of the cultures at 24 hours after treatment is shown.

FIG. 10A: Histological analysis. Cresyl violet staining of 50 μm coronal sections from control, 3-NP, and 3-NP+HSB-13-treated mice. Doses and conditions of administration are detailed in Methods. Top panels. Low magnification showing selective loss of cells in the striatum. Lower panels. High magnification image of dorsolateral part of the striatum. FIG. 10B: Analysis of locomotor activity. Locomotor activity measurements of mice administered with saline (control), 3-NP and 3-NP+ HSB13. Doses and conditions of administration are detailed in Methods. Activity was measured over a 15 min period. Shown are: A) total movement episodes; B) total movement distance; C) mean velocity; D) vertical plane entries. Bars indicate mean±SD.

DESCRIPTION OF THE INVENTION

Figure 1:
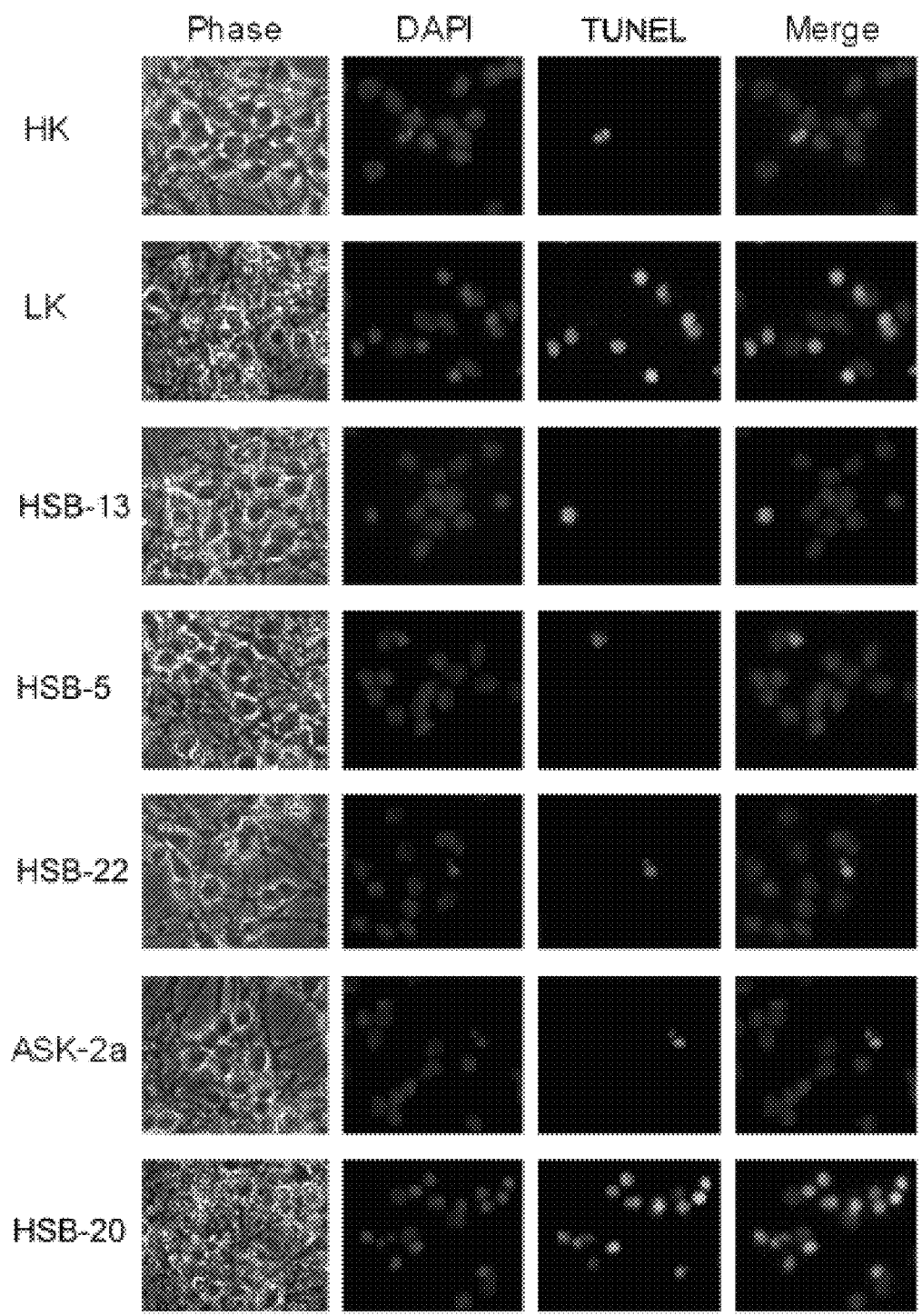
FIG. 1 is an image that shows 1,4-benzoxazine compounds protecting against LK-induced neuronal death. Cultures of cerebellar granule neuron were switched to HK medium, LK medium, or LK medium containing one of five 1,4-benzoxazine compounds—HSB-13, HSB-5, HSB-22, ASK-2a, and HSB-20. All compounds were used at 25 µM concentration. Viability was evaluated 24 h later by phase contrast microscopy, DAPI-staining (apoptotic neurons are detected by condensed or fragmented nuclei), or TUNEL-staining (apoptotic nuclei are labeled green). DAPI and TUNEL staining pictures are from the same field. While HSB-13, HSB-5, HSB-22 and ASK-2a were protective, HSB-20 was not.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Neurodegenerative diseases, such as Alzheimer's disease, Parkinson's disease, and amyotrophic lateral sclerosis (ALS), disrupt the quality of life for patients, put a tremendous burden on family caregivers, and cost society billions of dollars annually. The most consistent risk factor for developing neurodegenerative disease is aging. Because of the dramatic increase in life expectancy, the incidence of individuals afflicted with the aging-associated disorders is on the rise representing a major health problem. A commonality shared among this diverse set of disorders is the progressive and relentless loss of certain populations of neurons. Current medications for neurodegenerative diseases alleviate only the symptoms associated with these diseases but not affect the underlying cause, e.g., degeneration of neurons. Because neuronal loss continues unabated, such palliative treatments have no effect on disease progression. The identification of small-molecule inhibitors of neuronal death is thus of urgent and critical importance.

Neurodegenerative disorders, such as Alzheimer's disease (AD), are characterized by neurofibrillary tangles, neuritic plaques, and neuronal cell death. Alzheimer's is a degenerative and terminal disease for which there is no known cure and is characterized by plaques and tangles in the brain. In its most common form, it afflicts individuals over 65 years old, although a less prevalent early-onset form also exists. Neurodegenerative conditions strike an increasing number of individuals each year, and for many of these conditions conventional treatments offer little in the way of treatment. In some instances, the neurodegenerative conditions are associated specifically with a particular disease, such as multiple sclerosis, while in other instances the conditions are associated more generally with aging or some other condition or process of the body, such as a genetic disorder or an autoimmune disease, for example. These conditions, however, are characterized by weakness and impaired physical functions, and, sometimes, impaired mental functions as well.

The inventors have previously demonstrated that a cell-permeable chemical inhibitor of c-Raf called GW5074 {5-Iodo-3-[(3',5'-dibromo-4'-hydroxyphenyl)methylene]-2-indolinone}, completely inhibits the death of cultured neurons induced by a variety of different apoptotic stimuli (Chin et al., 2004). GW5074 also prevents striatal degeneration and improves behavioral performance in mice administered with 3-nitropropionic acid, a commonly used in vivo paradigm of Huntington's disease. GW5074 is a 3'substituted indolone (Chin et al., 2004). A number of other 3-substituted indolones have also been found to inhibit neuronal death (Johnson et al., 2005; Chen et al., 2008). Although highly protective, GW5074 as well as many other 3-substituted indolones display toxicity when used at higher concentrations (Chin et al., 2004; Johnson et al., 2005; Chen et al., 2008). A structure-activity relationship study has identified that additional 3-substituted indolones while being neuroprotective were also not toxic to cultured neurons even at high doses (Balderamos et al., 2008). Other investigators have similarly identified a number of chemical inhibitors of neuronal apoptosis targeting a variety of different pro-apoptotic proteins including c-jun N-terminal kinase (JNK), cyclin-dependent kinases (CDKs), glycogen synthase kinases (GSK3), and p53 (D'Mello et al., 2005).

The present invention provides several 1,4 benzoxazine derivatives that have therapeutic value and are neuroprotective in cultured cerebellar granule neurons induced to undergo apoptosis by potassium deprivation. Some of these compounds were also tested against oxidative stress and Aβ-induced neuronal death and found to be effective at non-toxic levels.

One of these compounds, designated as HSB-13, was tested in vivo in the 3-nitropropionic acid model of Huntington's disease. HSB-13 offered significant protection against neurodegeneration and improved locomotor performance in mice. HSB-13 was also protective against amyloid precursor protein (APP) induced toxicity in *Drosophila*. These studies identify 1,4-benzoxazine compounds as novel neuroprotective agents with therapeutic value against neurodegeneration.

Medications to ameliorate the symptoms associated with some neurodegenerative diseases are available, however, these kinds of therapies do not slow down disease progression because they do not stop the relentless degeneration of neurons. There is currently no strategy to stop the abnormal loss of neurons in neurodegenerative pathologies. Several candidate chemical compounds have been identified previously and many of these are in pre-clinical trials. A few have even been tested in human trials but unsuccessfully. Compounds of the 2-benzylidene-2H-1,4-benzoxazin-3-(4H)-one have never been tested as candidate drugs for the treatment of neurodegenerative pathologies.

The term "alkyl", "alkenyl", "alkynyl" and "alkylene" refers to hydrocarbon chains typically ranging from about 1 to about 12 carbon atoms in length, preferably 1 to about 6 atoms, and includes straight and branched chains. Unless otherwise noted, the preferred embodiment of any alkyl or alkylene referred to herein is $C_1$-$C_6$ alkyl (e.g., methyl or ethyl).

"Cycloalkyl" refers to a saturated or unsaturated cyclic hydrocarbon chain, including bridged, fused, or spiro cyclic compounds, preferably comprising 3 to about 12 carbon atoms, more preferably 3 to about 8.

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Heteroaryl" is an aryl group containing from one to four heteroatoms, preferably N, O, or S, or a combination thereof, which heteroaryl group is optionally substituted at carbon or nitrogen atom(s) with C1-C6 alkyl, —CF3, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1, 2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

"Heterocycle" or "heterocyclic" means one or more rings of 5-12 atoms, preferably 5-7 atoms, with or without unsaturation or aromatic character and at least one ring atom which is not carbon. Preferred heteroatoms include sulfur, oxygen, and nitrogen. Multiple rings may be fused "Heteroatom" means any non-carbon atom in a hydrocarbon analog compound. Examples include oxygen, sulfur, nitrogen, phosphorus, arsenic, silicon, selenium, tellurium, tin, and boron.

The term "alkylene" refers to a divalent alkyl group as defined above, such as methylene (—$CH_2$—), propylene (—$CH_2$ $CH_2$ $CH_2$—), chloroethylene (—$CHClCH_2$—), 2-thiobutene —$CH_2$ CH(SH)$CH_2$ $CH_2$, 1-bromo-3-hydroxyl-4-methylpentene (—$CHBrCH_2$ CH(OH)CH($CH_3$) $CH_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6-14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl.

The term "amido" denotes an amide linkage: —C(O)NHR (wherein R is hydrogen or alkyl).

The term "amino" denotes an amine linkage: —NR—, wherein R is hydrogen or alkyl. The term "carboxyl" denotes —C(O)O—, and the term "carbonyl" denotes —C(O)—.

The term "alkylcarboxyl" denote an alkyl group as defined above substituted with a C(O)O group, for example, $CH_3$C(O)O—, $CH_3$ $CH_2$C(O)O—, etc.

The term "carbocycle" means a cyclic hydrocarbon chain having about 5 to about 8 ring carbons such as cyclopentyl, cylcohexyl, etc. These groups can be optionally substituted with one or more functional groups as defined under "alkyl" above.

The term "halogen" includes chlorine, fluorine, bromine, iodine and mixtures thereof.

The term "heterocycle" means a straight chain or ring system that may contain from zero to four heteroatoms selected from N, O, and S, wherein the nitrogen and sulfur atoms are optionally oxidized, and the nitrogen atom(s) are optionally quaternized.

The term "carbamoyl" refers to the group —C(O)$NH_2$.

The term "hydroxyalkyl" means an alkyl group as defined above which is substituted by a hydroxy group.

The term "alkylcarbonyl", alone or in combination, means an acyl group derived from an alkanecarboxylic acid, i.e. alkyl-C(O)—, such as acetyl, propionyl, butyryl, valeryl, 4-methylvaleryl etc.

Unless indicated otherwise, all cell culture media and reagents were purchases from Invitrogen (Carlsbad, Calif.) and all chemicals were from Sigma-Aldrich (St. Louis, Mo.). Anhydrous solvents were purchased from Fischer Scientific (Pittsburgh, Pa.). PD98059, U0126, wortmannin, Akt inhibitor-X, trichostatin acid A (TSA), KN62, H89 were purchased from Calbiochem (La Jolla, Calif.). Antibodies used in this paper were as followed: anti-phospho-MEK (9121S), anti-phospho-AKT 473 (9271S), anti-phospho-GSK3α/β (9331S), c-Jun (2315S) were from Cell Signaling Technology (Beverly, Mass., USA); anti-ATF-3 (C-19, sc-188), anti-phospho-ERK (E-40, sc-7383), anti-α-tubulin (TU-02 sc-8035) were from Santa CruzBiotechnology (Santa Cruz, Calif., USA). All antibodies were used at a 1:1000 dilution.

Synthesis of 1,4-benzoxazine compounds. Compounds HSB-1-7, HSB-11, HSB-12, HSB-14, HSB-15, ASK-1 and ASK-2: The appropriate aldehyde (15 mmol) was added to a mixture of appropriate substituted 2H-1,4-benzoxazin-3 (4H)-one (10 mmol), acetic anhydride (4 ml) and triethylamine (2 ml). The reaction mixture was refluxed for 7 h, left overnight at room temperature and poured into crushed ice. The obtained solid was collected by filtration and washed with acetonitrile (70-88% yield). The crude product was purified by recrystallisation from ethanol. Compounds HSB-8, HSB-11, HSB-12, HSB 14-19, HSB-24, ASK-1 and ASK-2: The appropriate aldehyde (15 mmol) was added to a mixture of appropriate substituted 2H-1,4-benzoxazin-3(4H)-one (10 mmol), acetic anhydride (4 ml) and triethylamine (2 ml). The reaction mixture was refluxed for 7 h, left overnight at room temperature and poured into crushed ice. The obtained solid was collected by filtration and washed with acetonitrile (70-88% yield). The crude product was purified by recrystallisation from ethanol.

HSB-13: A catalytic amount of Raney nickel was added portion-wise with stirring to a mixture of HSB-1 (2 mmol) and hydrazine hydrate (1 ml) in ethanol (20 ml). The reaction mixture was refluxed fro 3 hours, and then filtered. The filtrate was evaporated to dryness under reduced pressure. The crude product was purified by recrystallisation from ethanol (70% yield).

HSB-23, HSB-25 and Ask-2a: The respective ester of these compounds (HSB-2, HSB-24 and ASK-2) (1 mmol) was treated with potassium carbonate (3 mmol) at 0° C. in methanol (10 ml) and stirred for 3 h at room temperature gave the respective alcohols HSB-23, HSB-25 and ASK-2a (70-75% yield).

HSB-22: Sodium methoxide was added in one portion to a mixture of 2H-1,4-benzoxazin-3(4H)-one (10 mmol) and pyrrole-2-carboxaldehyde (16 mmol) in dry DMF (10 ml). The reaction mixture was refluxed for 48 h, then cooled to room temperature and poured into crushed ice and left overnight at 4° C. The precipitated solid was collected by filtration, washed with water and dried. The precipitate was boiled with ethanol (150 ml) and filtered while hot to remove impurities. The filtrate was evaporated to dryness under reduced pressure, and residue was chromatographed on a silicagel column using (95:5) toluene: ethyl acetate as the mobile phase (21% yield).

HSB-9 and HSB-10: Sodium methoxide was added in one portion to a mixture of 2H-1,4-benzoxazin-3(4H)-one (10 mmol) and 4-dimethylamino benzaldehyde (16 mmol) in dry DMF (10 ml). The reaction mixture was refluxed overnight, then cooled to room temperature and poured into crushed ice and left overnight in the refrigerator. The precipitated solid was collected by filtration, washed with water and dried. The crude product was purified by recrystallisation from ethanol (30% yield) and DMF-ethanol (40% yield) respectively (40% yield).

HSB-20 and HSB-21: Sodium methoxide was added in one portion to a mixture of 2H-1,4-benzoxazin-3(4H)-one (10 mmol) and indole-3-carboxaldehyde (16 mmol) in dry DMF (10 ml). The reaction mixture was refluxed for 24 hours, then cooled to room temperature and poured into crushed ice and left overnight in the refrigerator. The precipitated solid was collected by filtration, washed with water and dried. The crude product was chromatographed on a silica gel column using (9:1) toluene: ethyl acetate (25-30% yield).

ASK-8, ASK-9 and ASK-11: A reaction mixture containing 2H-1,4-benzothazin-3(4H)-thione (2.7 mmol), an appropriate aldehyde (3.3 mmol) and catalytic amount of piperidine in dry benzene (10 ml) was stirred at 90° C. for 4 h, then cooled to room temperature. The crude product, which precipitated during cooling, was collected by vacuum filtration, washed with benzene, dried and purified by column chromatography on silica gel using ethyl acetate-hexane (1:4 v/v) (86-90% yield).

EXAMPLE 1

Reaction-1

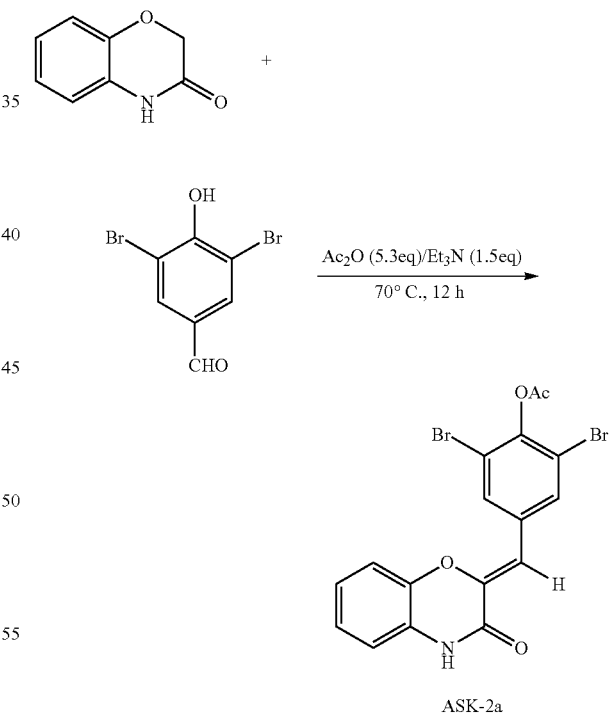

ASK-2a (Z)-2,6-Dibromo-4-((3-oxo-3,4-dihydro-2H-benzo[b][1, 4]oxazin-2-ylidene)methyl)phenyl acetate: A stirred mixture of (0.5 g, 3.35 mmol) of 2H-1,4-benzoxazin-3(4H)-one, 1.4 g of 4-hydroxy-3,5-dibromo benzaldehyde, 1.68 mL (17.729 mmol) of acetic anhydride and 0.7 mL (5 mmol) of triethyl amine was refluxed for 7 h, left overnight at room temperature and poured into crushed ice. The precipitated solid was collected by filtration and washed with acetonitrile. The crude product was purified by recrystallization from DMF: ethanol.

EXAMPLE 2

Reaction-2: (Z)-2-(3,5-Dibromobenzylidene)-2H-benzo[b][1,4]oxazin-3(4H)-one

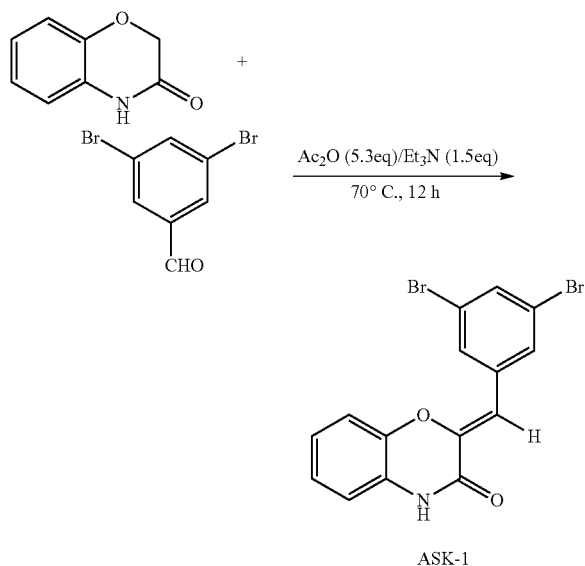

ASK-1

(Z)-2-(3,5-Dibromobenzylidene)-2H-benzo[b][1,4]oxazin-3(4H)-one. Chemical synthesis was the same as in Example 1, Reaction-1.

Culturing and treatments of cerebellar granule neurons: Granule neuron cultures were obtained from dissociated cerebella of 6-7 day old Wistar rats as described previously (D'Mello et al., 1993). Cells were plated in Basal Eagle's Medium (BME) supplemented with 10% fetal calf serum (FCS), 25 mM KCl, 2 mM glutamine (Invitrogen), and 100 µg/ml gentamycin in poly-L-lysine coated 24-well dishes at a density $1 \times 10^6$ cells/well. Cytosine arabinofuranoside (10 µM) was added to the culture medium 18-22 h after plating to prevent replication of nonneuronal cells. Previous immunocytochemical analyses by our lab and other investigators have shown that these cultures have high purity containing over 95% granule neurons (Thangnipon et al., 2003; Kingsbury et al., 2005).

The neuronal cultures were maintained for 7-8 days prior to treatment. For treatment, the cells were rinsed once and then maintained in low K+ medium (serum-free BME medium; referred to as LK), or in the case of control cultures, in high K+ medium (serum-free BME medium supplemented with 20 mM KCl; referred to as HK). For treatments, the chemical compounds (dissolved in dimethylsulfoxide) were added directly to LK medium at the time of the switch from HK at concentrations of 1, 5, or 25 µM. Viability was assessed 24 hours by 4',6'-diamidino-2-phenylindole hydrochloride (DAPI) staining (see below). Each compound was tested in duplicate (at each of the concentrations) and the experiment repeated at least 3 times.

The viability status of neuronal cultures treated with HK, LK, or LK medium supplemented with various compounds was evaluated by phase contrast microscopy and quantified by staining cell nuclei with DAPI as previously described (Yalcin et al., 2003; Morrison et al., 2006; Majzadeh et al., 2007)). Briefly, the cells were fixed in 4% paraformaldehyde for 20 min at 4° C. After washing in phosphate buffered saline, diamidino-2-phenylindole hydrochloride (DAPI; 1 µg/ml in phosphate buffered saline) was added for 15 min at room-temperature and viewed under ultraviolet light (260 nm). Cells with condensed or fragmented nuclei were scored as dead. Viability has been expressed as percent of control cultures, which were switched to HK medium). Statistical analysis was performed using an unpaired, two-tailed Student's T test, compared to mean neuronal survival of control cultures receiving LK treatment.

The mouse HT-22 neuroblastoma cell line was purchased from ATCC (Manassas, Va., USA) and cultured in Dulbecco's modified Eagle's medium (DMEM) with 4.5 g/L glucose (without sodium pyruvate) supplemented with 10% FBS, 100 units/ml penicillin and 100 µg/ml streptomycin. Cultures were plated at ~30% confluence for HCA treatment. HCA was made as 150 mM stock solution adjusted to pH 7.5 and used at a final concentration of 1.5 mM.

Primary cultures of cortical neurons were cultured from embryonic day 18 rats. The cultures were treated 1-2 days later with 5 uM of aged Aβ peptide (Aβ$_{25-35}$; purchased from Sigma-Aldrich). Neuronal viability was assayed 24 hours later.

The TUNEL assay of neuronal cultures was performed 24 h after treatment of the cultures using DEADEND™ Fluorometric TUNEL System from Promega (Madison, Wis.) according to the manufacturer's instructions. For immunocytochemical analysis of active caspase 3, neuronal cultures cells were fixed and treated with 0.2% Triton for 5 minutes. After blocking with PBS containing 5% BSA and 5% goat serum in PBS for 30, the coverslips were incubated with the active capase-3 primary antibody overnight at 4° C. After three washes with phosphate-buffered saline (PBS), the cells were incubated with secondary antibodies for 45 minutes at 25° C. after which the cells were washed with PBS. To visualize nuclei, cells were stained with DAPI for 15 minutes at 25° C.

The culture medium was removed and the cells were washed twice with ice-cold phosphate-buffered saline (PBS) and lysed in lysis buffer [1% Triton, 20 mM Tris-HCl (pH 7.5), 150 mM NaCl, 1 mM Na$_2$EDTA, 1 mM EGTA, 2.5 mM sodium pyrophosphate, 1 mM beta-glycerophosphate, 1 mM Na3VO4, 1 µg/mL leupeptin and 1 protease inhibitor mixture]. Protein concentrations were measured and normalized using Bradford protein assay reagent (Bio-Rad, Hercules, Calif., USA). Following normalization, 40 µg of protein was subjected to Western blotting. Immunoreactivity was examined by enhanced chemiluminescence (Amersham Bioscience, Piscataway, N.J., USA).

3-Nitropropionic acid administration and behavioral evaluation was done on 8-week old C57BL/6 male mice (Charles River Laboratories, Inc, Wilmington, Mass.) administered with 3-NP in ten intraperitoneal injections (50 mg/kg twice a day for 5 days) with or without HSB-13 (2 mg/kg). Injections of HSB-13 were performed 30 min before 3-NP administration. Control animals received saline injections. On the day following the 5 days of injection, locomotor activity was assessed using The TRU-SCAN® activity monitoring system (Coulborn Instruments, PA) as previously described (Chin et al., 2004; Chen et al., 2008b). The following behavioral parameters were selected: (1) Total movements time, (2) Total movement distance: the sum of all vectored X-Y coordinate changes in the floor plane, (3)Average distance per movement, (4) Mean velocity: the mean velocity of all X-T coordinate change defined movements.

Following behavioral evaluation, the mice were deeply anesthetized and brains removed. The brains were fixed in 4% paraformaldehyde in 0.1 M phosphate buffer and cryoprotected in 20% sucrose in 0.1 M phosphate buffer. Coronal sections were cut on a cryostat at 40 microns and stained with cresyl violet (Sigma-Aldrich) as previously described (Chin et al., 2004; Chen et al., 2008b).

Expression of human $APP_{695}$ was induced ubiquitously by crossing transgenic flies carrying a $UAS-APP_{695}$ construct (Fossgreen et al., 1998) with flies containing an actin-GAL4 promoter using the UAS/GAL4 system (Brand and Perrimon, 1993). Flies were raised at 25° C. in the dark on 10% yeast paste containing different concentrations of HSB-13 (0, 2.5, 5, and 50 µM). The percentage of surviving $APP_{695}$-expressing progeny was determined by comparing them to control progeny carrying no promoter construct obtained in the same cross and therefore raised under identical conditions as described previously (Greeve et al., 2004).

When cultured cerebellar granule neurons are switched from HK to LK medium about 50% of the cells underwent apoptosis within 24 h (D'Mello et al., 1993). The inventors utilized this widely used and recognized model to test a total of 20 different 1,4-benzoxazine derivatives for their ability to protect against LK-induced neuronal death. Each compound was tested at 3 different doses—1 µM, 5 µM and 25 µM and viability quantified by DAPI-staining. The highest does was included to test for possible toxicity effects of the compounds. Key results were confirmed using TUNEL staining, another reliable assay of apoptosis (FIG. 1). As shown in Table 1 and FIG. 1, the present invention identifies several compounds with significant neuroprotective effect. Two of the most protective compounds are HSB-13 and HSB-22, both with Ar=3',5'-dibromo-4'-hydroxyphenyl (FIG. 1). These compounds offer robust protection at 1 µM and protection is maintained at the two higher doses used in this study. Another compound displaying a high level of neuroprotection is ASK-2a (Ar=3',5'-dibromo-4'-hydroxyphenyl). Protection with this compound is lower than that observed with HSB-13 and HSB-22 at the two lower doses. Some compounds, including HSB-4, HSB-9, ASK-8, and ASK-9, showed maximal or near maximal efficacy at the 1 µM dose. To examine whether a higher level of protection could be observed at doses lower than 1 µM, the analyses of these compounds was extended to doses of 0.5, 0.25, and 0.1 µM. In all cases, protection was lower at these doses than what was observed at 1 µM. Thus, 1,4-benzoxazine compounds protected cultured neurons from apoptosis.

Figure 2:
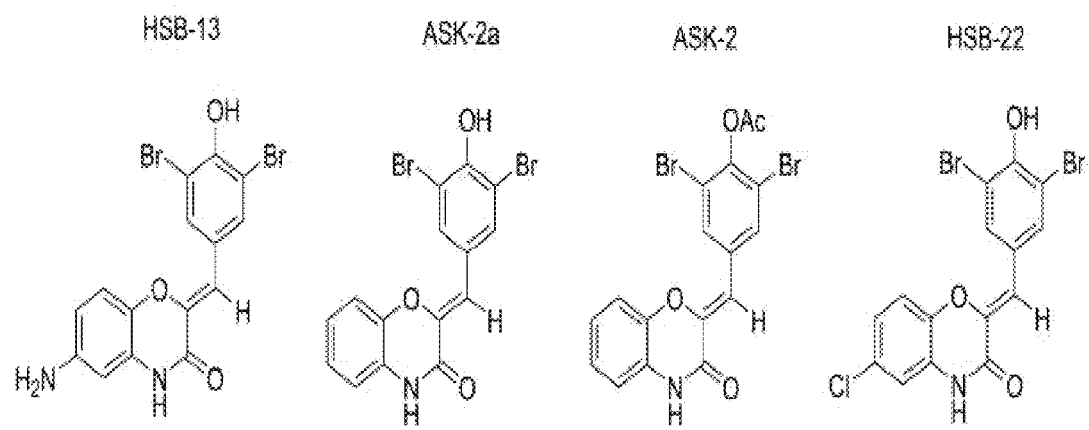
FIG. 2 is a schematic of some of the structures of four neuroprotective benzoxazines. The structures of HSB-13, ASK-2, ASK-2a, and HSB-13 are shown. As described in the text, ASK-2a displayed much higher neuroprotection than ASK2. HSB-13 displayed the highest neuroprotection.

Based on the structures of the compounds and the extent of neuroprotection they afford, the following conclusions can be drawn: (a) the somewhat higher level of protection observed with HSB-13 and HSB-22 when compared to ASK-2a which may be related to the absence of a substituent group at the 6-position in, (b) the importance of the 4'-OH in HSB-13, and HSB-22 is shown by the reduced protection by ASK2, which has an 4'-OAc group instead of the 4'-OH group (FIG. 2), and the lack of neuroprotection by the 3',5'-dibromo (ASK-1) and 3',4',5'-trimethoxy (HSB-6) derivatives, (c) with the exception of HSB-7 (pyridin-2-yl), which was protective at 5 µM, the heterocyclic derivatives i.e. HSB-11 (thiophen-2-yl), HSB-12 (thiophen-3-yl), HSB-4 (thiophen-3-yl) were inactive, and (d) conversion of the 4'-OH to a 4'-OCOCH3 ester gave mixed results. For example, compounds HSB-2 (6-Cl), HSB-5 (6-F) and HSB-3 (6-methyl) were highly protective at 25 µM and HSB-1 (6-nitro) was effective at 5 µM but not at the other two test concentrations. In comparison, the 4'-OH compounds, HSB-13 (6-NH2), HSB-22 (6-Cl) and ASK-2a (6-H) were effective in all the three concentrations.

Previous studies with 3-substituted indolones revealed that the substitution of C=O at the 2-position with C=S completely abolished neuroprotective activity (Balderamos et al., 2008). However, in the case of the benzoxazines included in the present invention, ASK-9 (pyrrol-2-yl and N-Me) and ASK-11 (2',5'-dimethoxyphenyl) showed a significant level of protection. However, ASK-8 (thiophen-2-yl) was inactive.

TABLE 1

Each of the 21 compounds were tested at 3 concentrations (1, 5, and 25 µM) and added to LK medium. Survival is represented at % survival in control cultures which received HK medium. Data represents mean values from at least 3 studies each of which was performed in duplicate. In LK medium without any additives, mean survival was 48%.

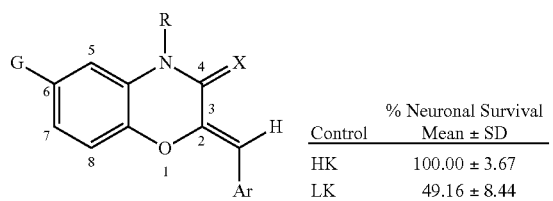

| Control | % Neuronal Survival Mean ± SD |
|---|---|
| HK | 100.00 ± 3.67 |
| LK | 49.16 ± 8.44 |

| | | | | | | % Survival | | |
|---|---|---|---|---|---|---|---|---|
| Entry | Compound | Ar | G | C=X | N—R | 1 µM | 5 µM | 25 µM |
| 1 | HSB-1 | 3,5-dibromo-4-acetoxyphenyl | NO$_2$ | O | H | 58.8 ± 10.31 | 96.5 ± 14.40* | 63.5 ± 9.34 |
| 2 | HSB-2 | 3,5-dibromo-4-acetoxy | Cl | O | H | 44.1 ± 23.42 | 62.3 ± 15.64 | 102 ± 9.85* |
| 3 | HSB-3 | 3,5-dibromo-4-acetoxy | Me | O | H | 56.9 ± 11.54 | 59.6 ± 11.97 | 97.4 ± 12.98* |
| 4 | HSB-4 | thiophen-3-yl | Me | O | H | 65.0 ± 4.34 | 60.3 ± 4.47 | 61.0 ± 3.58 |
| 5 | HSB-5 | 3,5-dibromo-4-acetoxyphenyl | F | O | H | 65.9 ± 5.08 | 69.3 ± 9.75 | 95.6 ± 0.98* |
| 6 | HSB-6 | 3,4,5-trimethoxyphenyl | I | O | H | 61.9 ± 9.07 | 72.1 ± 19.33 | 59.4 ± 13.11 |
| 7 | HSB-7 | pyridin-2-yl | Me | O | H | 59.4 ± 13.93 | 59.8 ± 6.40 | 88.1 ± 2.44* |
| 8 | HSB-9 | 4-dimethylamino phenyl | H | O | H | 67.3 ± 16.43 | 68.8 ± 13.54 | 63.3 ± 1.73 |
| 9 | HSB-11 | thiophen-2-yl | H | O | H | 64.2 ± 12.18 | 68.8 ± 4.26 | 68.8 ± 4.49 |
| 10 | HSB-12 | thiophen-3-yl | H | O | H | 76.8 ± 5.79* | 76.2 ± 3.42* | 81.4 ± 9.45* |
| 11 | HSB-13 | 3,5-dibromo-4-hydoxyphenyl | NH$_2$ | O | H | 87.35 ± 4.13* | 100.2 ± 2.25* | 95.1 ± 5.06* |
| 12 | HSB-14 | 3,4,5-trimethoxyphenyl | H | O | H | 63.9 ± 2.26 | 70.0 ± 1.63 | 69.2 ± 5.30 |
| 13 | HSB-15 | 3,4,5-trimethoxyphenyl | Me | O | H | 60.7 ± 2.76 | 66.5 ± 9.26 | 63.9 ± 3.32 |

TABLE 1-continued

Each of the 21 compounds were tested at 3 concentrations (1, 5, and 25 μM) and added to LK medium. Survival is represented at % survival in control cultures which received HK medium. Data represents mean values from at least 3 studies each of which was performed in duplicate. In LK medium without any additives, mean survival was 48%.

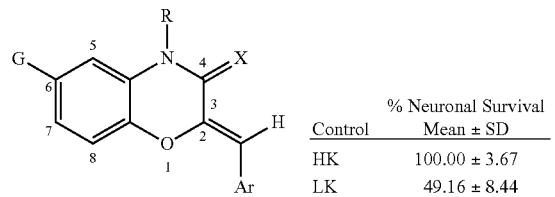

| Control | % Neuronal Survival Mean ± SD |
|---|---|
| HK | 100.00 ± 3.67 |
| LK | 49.16 ± 8.44 |

| | | | | | | | % Survival | | |
|---|---|---|---|---|---|---|---|---|---|
| Entry | Compound | Ar | G | C=X | N—R | 1 μM | 5 μM | 25 μM |
| 14 | HSB-20 | 3-indolyl | H | O | H | 52.2 ± 10.11 | 62.5 ± 3.14 | 48.3 ± 12.11 |
| 15 | HSB-22 | 3,5-dibromo-4-hydoxyphenyl | Cl | O | H | 82.59 ± 6.11* | 87.54 ± 8.83* | 91.24 ± 9.03* |
| 10 | ASK-1 | 3,5-dibromophenyl | H | O | H | 75.3 ± 10.56 | 68.8 ± 12.99 | 69.1 ± 7.56 |
| 17 | ASK-2 | 3,5-dibromo-4-acetoxyphenyl | H | O | H | 60.76 ± 8.83 | 66.59 ± 5.87 | 78.78 ± 1.19* |
| 18 | ASK-2a | 3,5-dibromo-4-hydroxyphenyl | H | O | H | 74.01 ± 6.93 | 80.84 ± 9.31* | 95.12 ± 3.28* |
| 19 | ASK-8 | thiophen-2-yl | H | S | H | 73.3 ± 0.79* | 60.8 ± 2.62 | 39.3 ± 7.78 |
| 20 | ASK-9 | pyrrol-2-yl | H | S | Me | 84.5 ± 3.30* | 70.2 ± 5.32 | 65.1 ± 5.63 |
| 21 | ASK-11 | 2,5-dimethoxy-phenyl | H | S | H | 73.8 ± 2.31 | 90.7 ± 14.50* | 74.0 ± 3.59 |

*p < 0.01 compared with viability of culture receiving LK.

Figure 3:
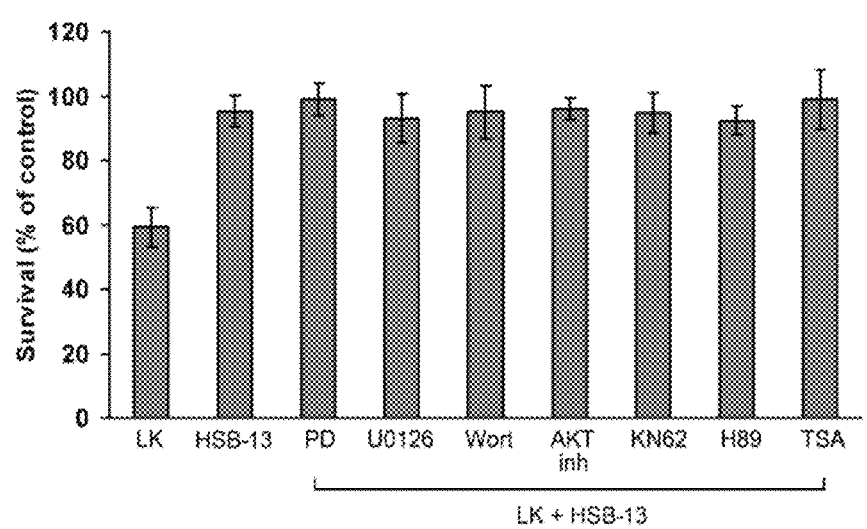
FIG. 3 is a plot that shows the effect of inhibition of signal transduction pathways on neuroprotection by 1,4-benzoxazines. Cultures of cerebellar granule neurons were switched to LK medium, LK medium containing of HSB-13, or LK medium containing HSB-13 and either PD98059 (40 µM), U0126 (10 µM), Wortmannin (100 nm), Akt inhibitor-X (5 µM), KN-62 (10 µM), H89 (10 µM) and TSA (1 µM). Viability was quantified 24 h later by DAPI staining. The results were normalized to viability in control cultures which were switched to HK medium.

The Raf-MEK-ERK and PI-3 kinase-Akt signaling are two well-established and powerful anti-apoptotic pathways in mammalian cells that mediate the protective effects of a number of neurotrophic polypeptides, pharmacological agents, and neuroprotective compounds (D'Mello and Chin, 2005; Hetman et al., 2006). To determine whether either of these pathways was involved in the neuroprotective effect of 1,4-benzoxazines the inventors studied whether the pharmacological inhibition of these pathways affected their neuroprotective efficacy. As shown in FIG. 3, neither PD98059, nor U0125, two structurally distinct and but highly selective MEK inhibitors, reduced neuroprotection by HSB-13. Similarly, none of the compounds tested (the PI-3 kinase inhibitor, wortmannin, the Akt inhibitor X, or a commercially available inhibitor of Akt) reduced the ability of HSB-13 to protect neurons against LK-induced apoptosis (FIG. 3). At the doses utilized in these studies, these inhibitors completely inhibit ERK or Akt stimulation resulting from HK-treatment. As observed for HSB-13, pharmacological inhibition of the MEK-ERK and PI-3K-Akt pathways had no effect on the neuroprotective actions of ASK-2a or HSB-22.

Figure 4:
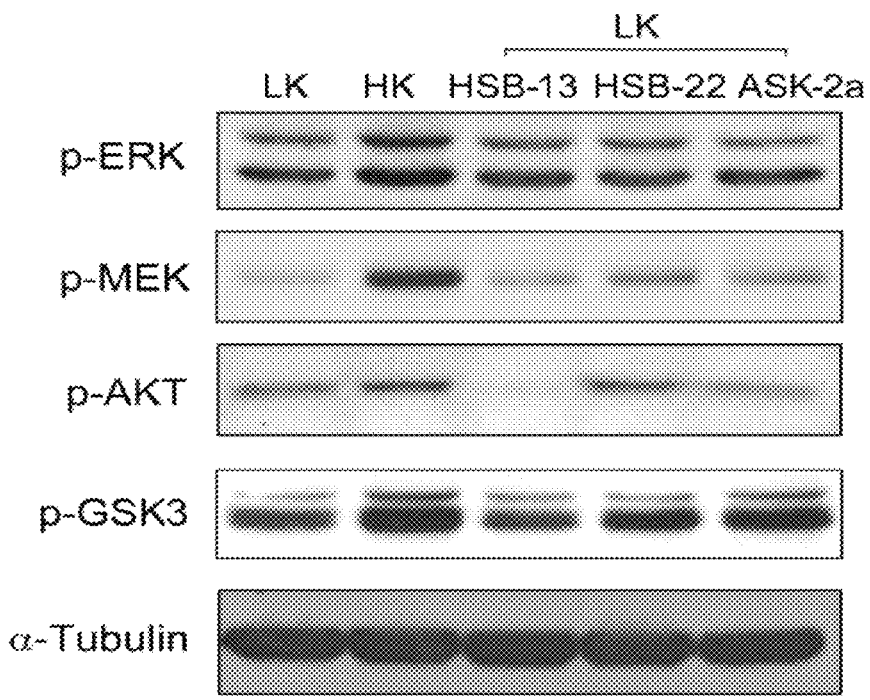
FIG. 4 is an image that shows the Western blot analysis of signaling proteins in neuronal cultures treated with protective 1,4-benzoxazine compounds. Cultures of cerebellar granule neurons were switched to HK medium, LK medium, or LK medium containing of HSB-13, HSB-22, or ASK-2a for 3 h. Total cell lysates were prepared and analyzed by Western blotting using antibodies against phospho-Akt (Ser473), phospho-MEK, phospho-ERK, and phospho-GSK3β. An antibody against α-tubulin was also used to show that similar amounts of lysate were loaded in each lane.

A Western Blot Analysis was performed to confirm that neuroprotection by 1,4-benzoxazines does not involve activation of MEK-ERK or PI3 kinase-Akt signaling. Activation of MEK, ERK and Akt requires their phosphorylation, which can be detected using phospho-specific antibodies. As previously reported by the inventors and others (Chin et al., 2004; Johnson et al., 2005; Majdzadeh et al., 2008), MEK and ERK phosphorylation decreases following LK treatment of cerebellar granule neurons. This decrease is not prevented by HSB-13, HSB-22, or ASK-2a (FIG. 4). Phosphorylation of Akt at Ser473 is also slightly decreased at 6 hr of LK treatment (Chin et al., 2004; Johnson et al., 2005; Majdzadeh et al., 2008). This is also not affected by treatment with ASK-2a or HSB-22 (FIG. 4). HSB-13, however, inhibits Akt (Ser473) phosphorylation even more than that seen in LK. The striking difference in phosphorylation pattern between HSB-13 and the two other neuroprotective compounds suggests that HSB-13 affects signaling molecules differently from HSB-22 and ASK-2a.

Since the Raf-MEK-ERK and the PI-3 Kinase-Akt pathways are not required for neuroprotection by HSB-13, the involvement of other signaling molecules that are known to promote neuronal survival was determined. GSK3β is a proapoptotic molecule that is activated during apoptosis in many neuronal and non-neuronal systems. Under survival promoting conditions GSK3β is kept inactivated by phosphorylation at an inhibitory site, a modification that can be induced by Akt as well as by other kinases. As shown in FIG. 4, dephosphorylation of GSK3β is not inhibited by HSB-13. In comparison, HSB-22 and ASK-2a inhibit dephosphorylation of GSK3β.

Treatment of cerebellar granule neurons with HK activates calcium-calmodulin kinase (CaMK) and inhibition of CaMK with pharmacological inhibitors such as KN-62 inhibits HK-mediated survival (See et al., 2001; Linseman et al., 2003; Morrison et al., 2006). Neuroprotection by HSB-13 is not, however, reduced by KN-62 treatment (FIG. 3). The present inventors recognized that several investigators have shown that cyclic AMP analogs and pharmacological activators of protein kinase A promote survival of cerebellar granule neurons as well as other neuronal types in the absence of other survival-promoting stimuli (Rydel and Greene, 1988; D'Mello et al., 1993; Hanson et al., 1998). PKA-mediated neuronal survival is blocked by treatment with H89, a potent and selective PICA inhibitor (Li et al., 2000; Bhave and Hoffman, 2004). As shown in FIG. 3, treatment with H89 has no effect on HSB-13 mediated neuroprotection. The inventors have previously reported that histone deacetylase inhibitors such as trichostatin A block the ability of HK to maintain the survival of cerebellar granule neurons (Salminen et al., 1998; Boutillier et al., 2002; Morrison et al., 2006). However, TSA treatment also did not inhibit the neuroprotective efficacy of HSB-13 significantly (FIG. 3).

Figure 5:
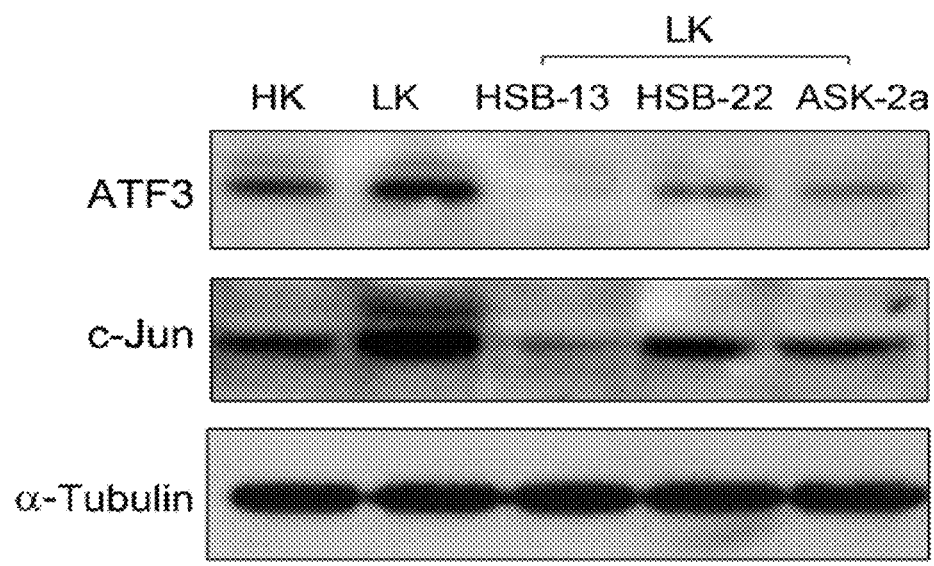
FIG. 5 is an image that shows the effect of benzoxazines on c-jun and ATF-3 expression. Cerebellar neuron cultures were treated for 3 h with HK, LK, or LK medium containing 25 µM HSB-13, 25 µM ASK-2a, or 25 µM HSB-22. Whole cell lysates were then prepared and subjected to Western blot analysis using antibodies against c-jun and ATF-3. An antibody against α-tubulin was also used to show that similar amounts of lysate were loaded in each lane.

C-jun expression is induced in a variety of tissue culture and in vivo paradigms of neuronal apoptosis (Schenkel et al., 2004). The activation of this transcription factor has been shown to be necessary for neuronal death in LK-induced cerebellar granule neurons as well as other models of neuronal death (Estus et al. 1994; Ham et al. 1995; Watson et al. 1998). As shown in FIG. 5, induction of c-jun expression by LK is inhibited by HSB-13, HSB-22, and ASK-2a. Treatment with HSB-13 inhibited c-jun expression even lower that that seen in HK-treated cultures. Another transcription factor whose expression is stimulated in neurons during apoptosis is ATF-3, a member of the CREB family of proteins, which has been shown to promote neuronal death in different models (Hai et al. 1999; Vlug et al. 2005; Chen et al., 2008a). The suppression of ATF-3 expression using siRNA inhibits LK-mediated death of cerebellar granule neurons has been previously been described by the present inventors (Chen et al., 2008a). As shown in FIG. 5, the LK-mediated increase in ATF-3 is inhibited by all three neuroprotective benzoxazines. As observed with c-jun, the suppression was most robust with HSB-13. As a result these compositions can inhibit the activity of c-jun and ATF-3, which in turn play a role in treating cancer and oncoproteins like c-jun.

Figure 6A:
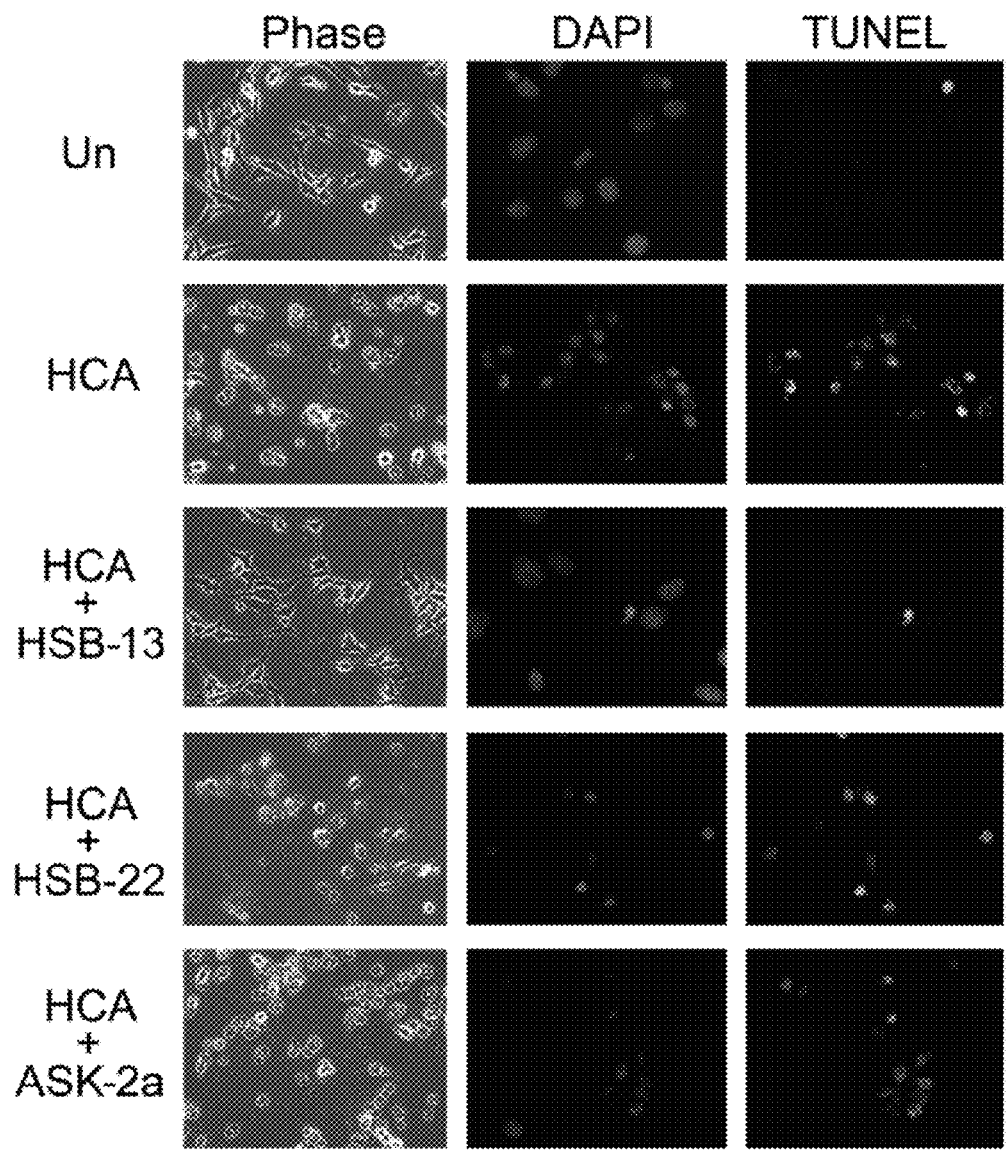
FIGS. 6A and 6B show the effects of HSB-13 on HT-22 cells and the quantification of cell death.
Figure 6B:
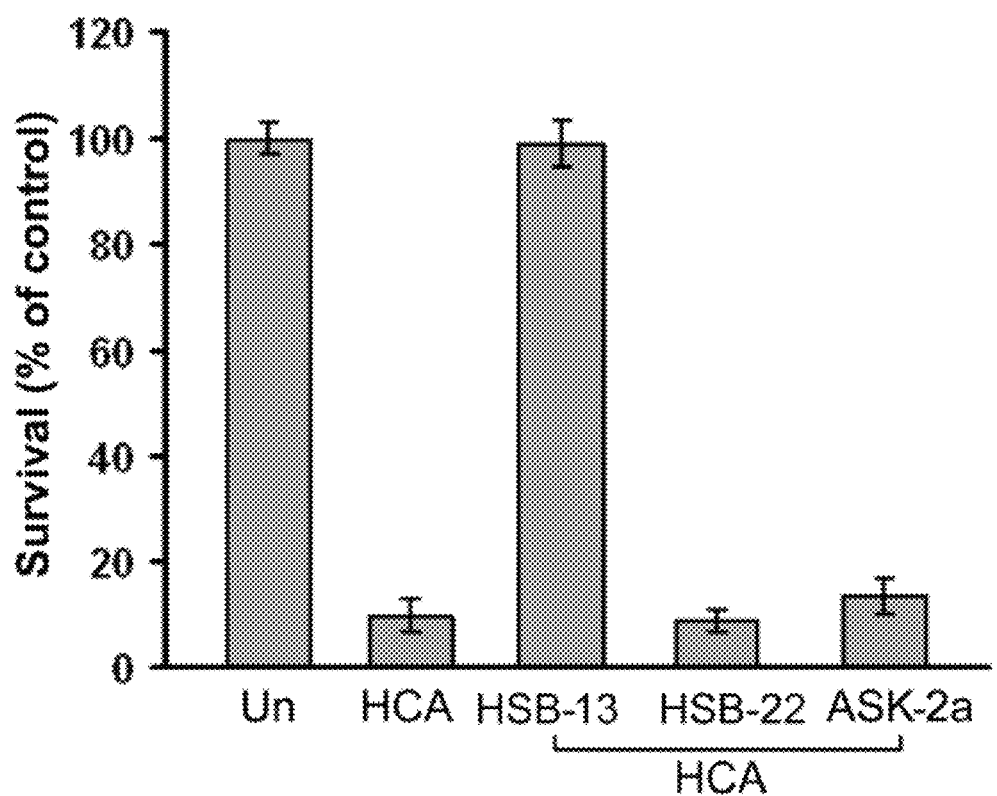

Treatment of the mouse neuroblastoma HT-22 cell line with homocysteic acid (HCA) induces apoptosis through glutathione depletion and oxidative stress (Murphy et al. 1990; Ratan et al. 1994a, 1994b). The inventors studied whether HSB-13, HSB-22, and ASK-2a were protective in this paradigm of oxidative stress-induced neuronal death. As shown in FIGS. 6A and 6B. HSB-13 prevents HCA-induced cell death. Although highest protection was observed at 25 µM concentration, HSB-13 also afforded robust protection at 5 µM. Surprisingly, given their structural similarity, ASK-2a and HSB-22 failed to protect at any of the three doses examined (data not shown). The finding that all three benzoxazines protect against LK-mediated neuronal death, but only HSB-13 is protective against HCA-induced apoptosis suggests that the molecular mechanisms underlying apoptosis in these two paradigms are different. Moreover, this result suggests that that the amino group at the 6-position (see FIG. 2) is necessary for protection against HCA toxicity. We have also found that HSB-13 protects primary cultures or cortical neurons against Aβ toxicity. Thus, HSB-13, but not ASK-2a and HSB-22, is protective against oxidative stress-induced neuronal death.

Figure 7A:
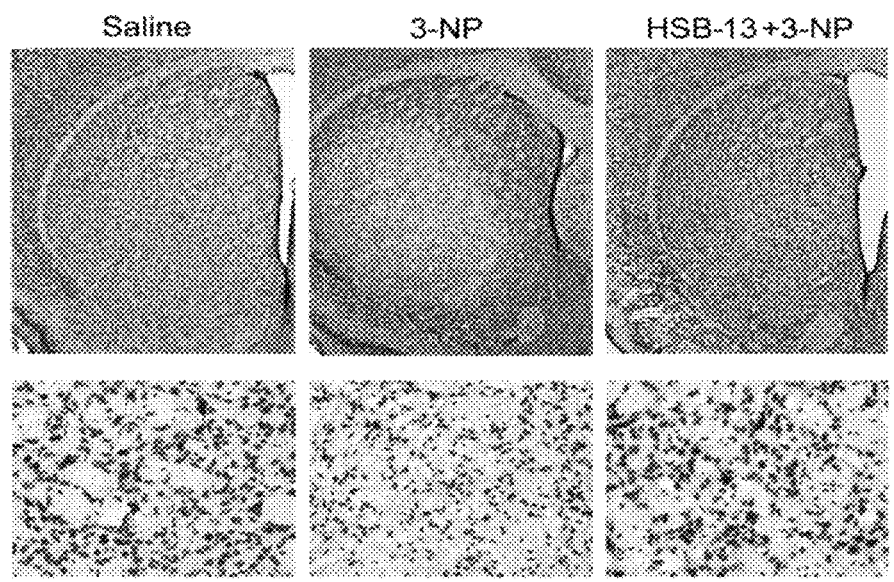
FIGS. 7A and 7B show the effects of HSB-13 in neural protection and locomotive activity.
Figure 7B:
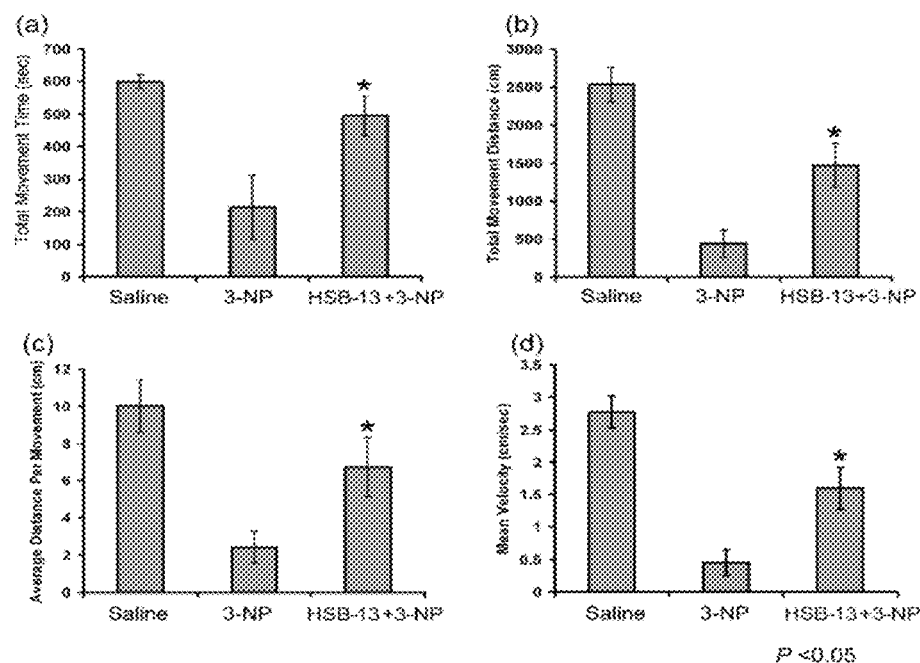

Cerebellar granule neuronal cultures and HT-22 cells showed that that HSB-13 has a strong and versatile neuroprotective efficacy in tissue culture paradigms. Nitropropionic acid (3-NP) administration in rodents and nonhuman primates replicates most of the clinical and pathophysiological hallmarks of HD including selective striatal degeneration, spontaneous choreiform and dystonic movements. Administration of this neurotoxin thus serves as a useful model for HD (Brouillet et al., 1999). The present inventors investigated the efficacy of HSB-13 in this in vivo paradigm. As shown in FIG. 7A, mice administered with 3-NP displayed extensive striatal lesions. This degeneration is substantially reduced by HSB-13 when administered at a concentration of 2 mg/kg body weight (FIG. 7A). The protection by HSB-13 against 3-NP-induced striatal neurodegeneration correlated with a significant improvement of locomotor performance (FIG. 7B). Specifically, total movement time; total movement distance; average distance per movement and mean velocity of movement, which were all impaired by 3-NP administration, were markedly higher in animals receiving HSB-13, proving that HSB-13 is neuroprotective in an in vivo model of Huntington's disease (HD).

Figure 8:
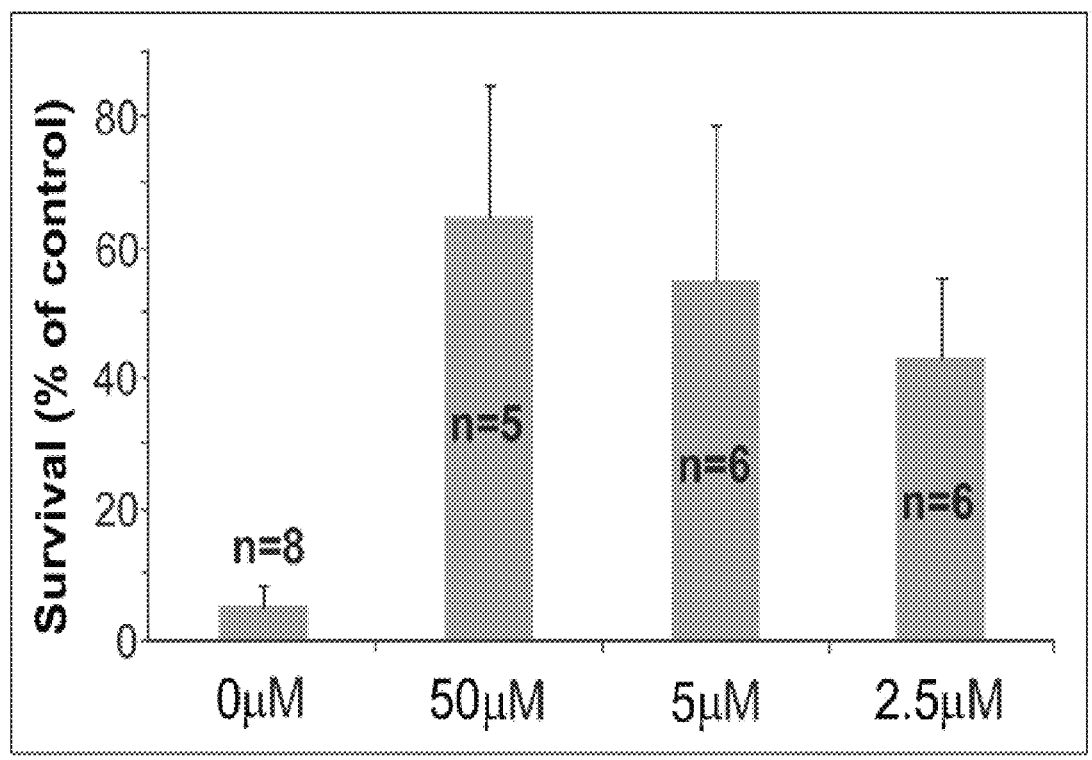
FIG. 8 is an image that shows that HSB-13 protects against $APP_{695}$-induced toxicity in *Drosophila*. Survival of flies expressing human $APP_{695}$ compared to controls. Treatment with HSB-13 significantly increased the survival rate of APP expressing flies. n=number of independent studies with groups of 15-20 flies. Bars indicate mean±SEM.

The present inventors also studied the beneficial effects of HSB-13 on APP-induced toxicity, by using a fly model expressing $APP_{695}$ ubiquitously (Greeve et al., 2004). As shown in FIG. 8, untreated flies show a survival rate of only about 5% compared to control flies raised under the same conditions that do not express $APP_{695}$. Raising these flies on food containing increased concentrations of HSB-13 resulted in a significant increase in the survival rate of APP-expressing flies ranging from 65% at 50 µM to 44% at 50 µM compared to equally treated control flies. These survival rates are approximately 10 times higher compared to untreated flies (all p-values<0.05) showing that HSB-13 also protects against APP-induced toxicity in a *Drosophila* in vivo model.

Thus, the present invention describes several novel compounds that are protective against LK-induced apoptosis of cerebellar granule neurons. The focus of the present invention has been on three of these compounds—HSB-13, HSB-22 and ASK-2a. Although structurally similar, only one of these compounds, HSB-13, is protective against HCA-induced toxicity of hippocampal neuroblastoma HT22 cells. ASK-2a and HSB-22 provide impressive neuroprotection in primary granule neurons, suggesting that they are likely to be efficacious in other paradigms of neuronal death in which oxidative stress is not a critical component. In addition to LK and HCA-induced cell death, HSB-13 protects primary cortical neurons against Aβ-induced toxicity and HCA-toxicity. The increased versatility of HSB-13 can be attributed to a single substituent group—the presence of an amino group at position 6.

The data provided herein also demonstate that HSB-13 is also protective in two separate in vivo models of neurodegeneration. Indeed, HSB-13 reduced striatal degeneration and improves behavioral performance in a chemically-induced mouse model of Huntington's disease and it protects against APP-toxicity in flies. Its effectiveness in tissue culture as well as in in vivo paradigms of neurodegeneration suggests that HSB-13 or derivatives of it could have value as therapeutic drugs in the treatment of human neurodegenerative conditions.

Studies by the present inventors suggest that PI-3 kinase—Akt and Raf-MEK-ERK signaling pathways, or other molecules involved in HK-mediated neuronal survival such as CaMK, PKA, and HDACs, are not involved in the ability of these compounds to protect suggesting a distinct mechanism of action. The studies, however, indicate that these compounds inhibit the activation of ATF-3 and c-jun although the upstream mechanisms by which this is mediated remain to be delineated. As observed with its ability to protect against HCA-induced toxicity, the effect of HSB-13 on some of the signaling molecules is qualitatively different from those elicited by HSB-22 or Ask-2a treatment. For example, the suppression of ATF-3 and c-jun is much more robust with HSB-13 as compared to that seen with HSB-22 and ASK-2a. HSB-13 is also the only compound that inhibits the phosphorylation of Akt at Ser473. And the extent of GSK3 activation, as judged by its dephosphorylation, is higher with HSB-13 than with HSB-22 and ASK-2a. It is possible that some of these differences may explain why HSB-13, but not HSB-22 or ASK-2a, is protective against HCA-induced toxicity.

To better understand the mechanism of action of the compounds of the present invention, but in no way a limitation; the effects of HSB-13 and ASK-2a on 20 different kinases were examined in vitro. The results of the study are presented in Tables 2 and 3. At 500 nM concentration, ASK-2a inhibited the kinase activities of GSK3α, GSK3β, p38α, p38β, JNK3, MLK3, and B-Raf substantially. In addition to inhibiting the above mentioned kinases, HSB-13 also inhibited CDK1, CDK2, CDK5 as well as ROCK1 when used at 500 nM. Both compounds displayed the strongest inhibition against p38β. As described above, ASK-2a protects cerebellar granule neurons against LK-induced death but is ineffective against HCA-induced toxicity of HT-22 cells. In contrast, HSB-13 is protective in both paradigms. This indicates that the protective effect of HSB-13 in HCA-treated HT-22 cultures is due to its inhibitory effect on the CDKs. Previous studies have established that CDK inhibitors can protect neurons against a number of different apoptotic stimuli.

At 100 nM, HSB-13 is considerably more selective at inhibiting GSK3α, GSK3β, p38β and B-Raf. GW5074, a 3-substituted indolone with strong neuroprotective effects also inhibits B-Raf. Although GW5074 inhibits GSK3β weakly, the finding that B-Raf is inhibited by structurally distinct neuroprotective compounds implicates the inhibition of this kinase as key event in the molecular mechanisms underlying neuroprotection.

Table 2: Effect of ASK-2a at 500 nM on 20 different kinases measured in vitro. Kinase activity is expressed as a percentage of that in control assays (without ASK-2a). The values are mean of assays performed in duplicate. Substantial inhibition of kinase activity (>20%) is in bold type.

TABLE 2

Effect of ASK-2a at 100 nM and 500 nM on 20 different kinases measured in vitro.

| | % ACTIVITY | |
|---|---|---|
| KINASES | 100 nM | 500 nM |
| GSK3α | 71 | 41 |
| GSK3β | 55 | 35 |
| p38α | 76 | 62 |
| p38β | 33 | 13 |
| CDK1/Cylcin A1 | 101 | 88 |
| CDK1/Cyclin B1 | 91 | 98 |
| CDK2/Cyclin A1 | 104 | 100 |
| CDK5/p25 | 100 | 96 |
| CDK4/Cyclin D1 | 93 | 97 |
| CDK6/Cyclin D3 | 104 | 99 |
| ROCK1 | 96 | 98 |
| JNK2 | 95 | 93 |
| JNK3 | 94 | 70 |
| LRRK2 | 96 | 94 |
| ASK1 | 104 | 97 |
| DAPK1 | 98 | 95 |
| MLK3 | 88 | 49 |
| B-Raf | 79 | 66 |
| c-Raf | 92 | 88 |
| MEKK1 | 100 | 98 |

The activity of each kinase was measured in vitro in the presence either 100 nM or 500 nM ASK-2a. Kinase activity is expressed as a percentage of that in control assays (without ASK-2a). The values are mean of assays performed in duplicate. Substantial inhibition of kinase activity (>20%) is in bold type.

It was found that with HSB-13: GSK3α, GSK3β, p38β, and B-Raf are efficiently inhibited (at 100 nM concentration). Also inhibited were: CDK1, CDK2, ROCK1, JNK2, MLK3, and c-Raf (all these are inhibited at 500 nM). Using ASK2a it was found that: GSK3α, GSK3β, p38α, p38β, JNK3, and B-Raf are inhibited efficiently (at 100 nM), while MLK3 is inhibited less efficiently. Therefore, kinases that are targets of 1,4-benzoxazines include GSK3α, GSK3β, p38α, p38β, B-Raf, CDK1, CDK2, JNK2, JNK3, and MLK3.

Table 3: Effect of HSB-13 at 500 nM on 20 different kinases measured in vitro. Kinase activity is expressed as a percentage of that in control assays (without HSB-13). The values are mean of assays performed in duplicate. Substantial inhibition of kinase activity (>20%) is in bold type.

TABLE 3

Effect of HSB-13 at 100 nM and 500 nM on 20 different kinases measured in vitro.

| | % ACTIVITY | |
|---|---|---|
| KINASES | 100 nM | 500 nM |
| GSK3α | 60 | 23 |
| GSK3β | 53 | 19 |
| p38α | 88 | 43 |
| p38β | 45 | 10 |
| CDK1/Cylcin A1 | 95 | 61 |
| CDK1/Cyclin B1 | 90 | 79 |
| CDK2/Cyclin A1 | 82 | 40 |
| CDK5/p25 | 84 | 56 |
| CDK4/Cyclin D1 | 103 | 88 |
| CDK6/Cyclin D3 | 99 | 89 |
| ROCK1 | 91 | 75 |
| JNK2 | 98 | 75 |
| JNK3 | 92 | 92 |
| LRRK2 | 97 | 88 |
| ASK1 | 104 | 95 |
| DAPK1 | 96 | 84 |
| MLK3 | 94 | 55 |
| B-Raf | 72 | 43 |
| c-Raf | 97 | 74 |
| MEKK1 | 99 | 98 |

It was found that 1,4-benzoxazine compounds protect cultured neurons from apoptosis. When cultured cerebellar granule neurons are switched to LK medium, about 50% of the cells undergo apoptosis within 24 h. In this study, a total of 20 different 1,4-benzoxazine derivatives of the structure shown in FIG. 1 were tested for their ability to protect against LK-induced death of cerebellar granule neurons. Each compound was tested at 3 different doses —1 μM, 5 μM and 25 μM. Neuronal viability was quantified by DAPI-staining, a common and reliable assay of apoptotic cell death. The results of the effects of the on neuronal death have been compiled in TABLE 4. In some cases, the results obtained from DAPI-staining were confirmed by two other assays of apoptosis— TUNEL staining and active caspase-3 immunocytochemistry.

TABLE 4

| | | | | | | % Survival. | | |
|---|---|---|---|---|---|---|---|---|
| Entry | Compound | Ar | G | C=X | N—R | 1 μM | 5 μM | 25 μM |
| 1 | HSB-1 | 3,5-dibromo-4-acetoxyphenyl | $NO_2$ | O | H | 58.8 ± 10.31 | 96.5 ± 14.40* | 63.5 ± 9.34 |
| 2 | HSB-2 | 3,5-dibromo-4-acetoxy | Cl | O | H | 44.1 ± 23.42 | 62.3 ± 15.64 | 102 ± 9.85* |
| 3 | HSB-3 | 3,5-dibromo-4-acetoxy | Me | O | H | 56.9 ± 11.54 | 59.6 ± 11.97 | 97.4 ± 12.98* |
| 4 | HSB-4 | thiophen-3-yl | Me | O | H | 65.0 ± 4.34 | 60.3 ± 4.47 | 61.0 ± 3.58 |
| 5 | HSB-5 | 3,5-dibromo-4-acetoxyphenyl | F | O | H | 65.9 ± 5.08 | 69.3 ± 9.75 | 95.6 ± 0.98* |
| 6 | HSB-6 | 3,4,5-trimethoxyphenyl | I | O | H | 61.9 ± 9.07 | 72.1 ± 19.33 | 59.4 ± 13.11 |
| 7 | HSB-7 | pyridin-2-yl | Me | O | H | 59.4 ± 13.93 | 59.8 ± 6.40 | 88.1 ± 2.44* |
| 8 | HSB-9 | 4-dimethylamino phenyl | H | O | H | 67.3 ± 16.43 | 68.8 ± 13.54 | 63.3 ± 1.73 |

TABLE 4-continued

| | | | | | | | % Survival. | |
|---|---|---|---|---|---|---|---|---|
| Entry | Compound | Ar | G | C=X | N—R | 1 µM | 5 µM | 25 µM |
| 9 | HSB-11 | thiophen-2-yl | H | O | H | 64.2 ± 12.18 | 68.8 ± 4.26 | 68.8 ± 4.49 |
| 10 | HSB-12 | thiophen-3-yl | H | O | H | 76.8 ± 5.79* | 76.2 ± 3.42* | 81.4 ± 9.45* |
| 11 | HSB-13 | 3,5-dibromo-4-hydoxyphenyl | NH$_2$ | O | H | 83.1 ± 4.53* | 100.8 ± 0.07* | 99.5 ± 1.56* |
| 12 | HSB-14 | 3,4,5-trimethoxyphenyl | H | O | H | 63.9 ± 2.26 | 70.0 ± 1.63 | 69.2 ± 5.30 |
| 13 | HSB-15 | 3,4,5-trimethoxyphenyl | Me | O | H | 60.7 ± 2.76 | 66.5 ± 9.26 | 63.9 ± 3.32 |
| 14 | HSB-20 | 3-indolyl | H | O | H | 52.2 ± 10.11 | 62.5 ± 3.14 | 48.3 ± 12.11 |
| 15 | HSB-22 | 3,5-dibromo-4-hydoxyphenyl | Cl | O | H | 91.9 ± 1.98* | 96.7 ± 2.96* | 90.6 ± 0.84* |
| 16 | ASK-1 | 3,5-dibromophenyl | H | O | H | 75.3 ± 10.56 | 68.8 ± 12.99 | 69.1 ± 7.56 |
| 17 | ASK-2 | 3,5-dibromo-4-acetoxyphenyl | H | O | H | 80.8 ± 13.67 | 92.2 ± 6.42* | 102.5 ± 10.2* |
| 18 | ASK-8 | thiophen-2-yl | H | S | H | 73.3 ± 0.79* | 60.8 ± 2.62 | 39.3 ± 7.78 |
| 19 | ASK-9 | pyrrol-2-yl | H | S | Me | 84.5 ± 3.30* | 70.2 ± 5.32 | 65.1 ± 5.63 |
| 20 | ASK-11 | 2,5-dimethoxy-phenyl | H | S | H | 73.8 ± 2.31 | 90.7 ± 14.50* | 74.0 ± 3.59 |

Table 4 provides 20 compounds each of which were tested at 3 concentrations (1, 5 and 25 µM) and added to LK medium. Survival is represented at % of survival in control cultures which received HK medium. Data represent mean values from at least 3 experiments each of which was performed in duplicate. In LK medium without any additives, mean survival was 48.16±8.44%. The compounds had the basic structure listed below with the substitutions as listed in Table 4.

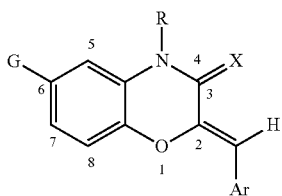

Although a detailed structure-activity relationship has not been performed our analysis of the 20 compounds suggests the following: (1) the parent compound (see TABLE-4 for core structure), the most effective neuroprotecting compounds is ASK-2 (Ar=3,5-dibromo-4-hydroxypuenyl). As shown in the Table 4, ASK-2 is highly protecting at 25 µM (102.5%) and 5 µM (92.1%) but only moderately protecting at 1 µL (80.3%. The importance of the 4-OH is shown by the lack of neuroprotection by the 3,5-dibromo (ASK-1) and 3,4,5-trimethoxy (HSB-6) derivatives. With the exception of HSB-7 (pyridyl-3-yl), which was moderately active (88%) in 5 µM, the parent heterocyclic derivatives i.e. ASK-9 (thiophen-2-yl), HSB-4 (thiophen-3-yl) were inactive. (2) Substitution at the 6-position of ASK-2 with an amino group [HSB-13] or chloro atom [HSB-22] results in improved activity at certain concentrations. For example, HSB-22 is highly protecting at all concentrations, i.e. 92%, 97% and 90.6% at 1 µM, 5 µM and 25 µM, respectively. Compound HSB-13 was significantly more effective (100.8%) than ASK-2 (92.2) at 5 µM and nearly as effective (99.5) as ASK-2 (102.5) at 25 µM. (3) Substitution at the 7-position on the neutroprotecting ability of the titled compounds is much less pronounced as compared to 6-substitution. Only one concentration is highly active. For example, Compounds HSB-2 (7-Cl), HSB-5 (7-F) and HSB- (7-methyl) were highly protective (~97%) in 25 µM solutions and HSB-1 (7-nitro) was effective at 5 µM. All four were not effective in the other two test solutions. (4) Substitution of C=O by C=S gives mixed results. In this study ASK-9 (pyrrol-2-yl and N-Me) was moderate activity (84.5%) at 1 µM and ASK-11 (2,5-dimethoxyphenyl) was highly active (90.7%) at 5 µM. However, ASK-8 (thiophen-2-yl) inactive.

Figure 9:
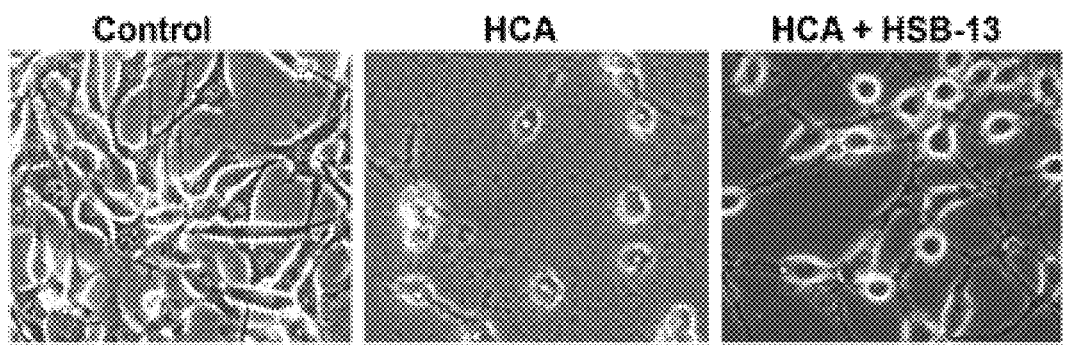
FIG. 9 is an image of that shows HSB-13 protects HT-22 cells against HCA-induced toxicity. HT-22 cells were treated with no additives (Control), 2 mM HCA, or 2 mM HCA+25 μM HSB-13. The appearance of the cultures at 24 h after treatment is shown.

Analysis in cultured cerebellar granule neurons identified HSB-13 as one with strong neuroprotective efficacy. We therefore selected HSB-13 to examine whether its protective effects extended to other neuronal types and apoptotic stimuli. Treatment of the hippocampally-derived neuroblastoma cell line, HT-22, with homocysteic acid (HCA) causes oxidative stress due to glutathione depletion leading to apoptosis (Murphy et al., 1990; Ratan et al., 1994a and 1994b). As shown in FIG. 9, treatment with 2 mM HCA resulted in almost complete cell death at 24 h which was prevented by HSB-13 at 25 uM concentration. HSB-13 was not protective when used at 5 uM in this paradigm.

Figure 10:
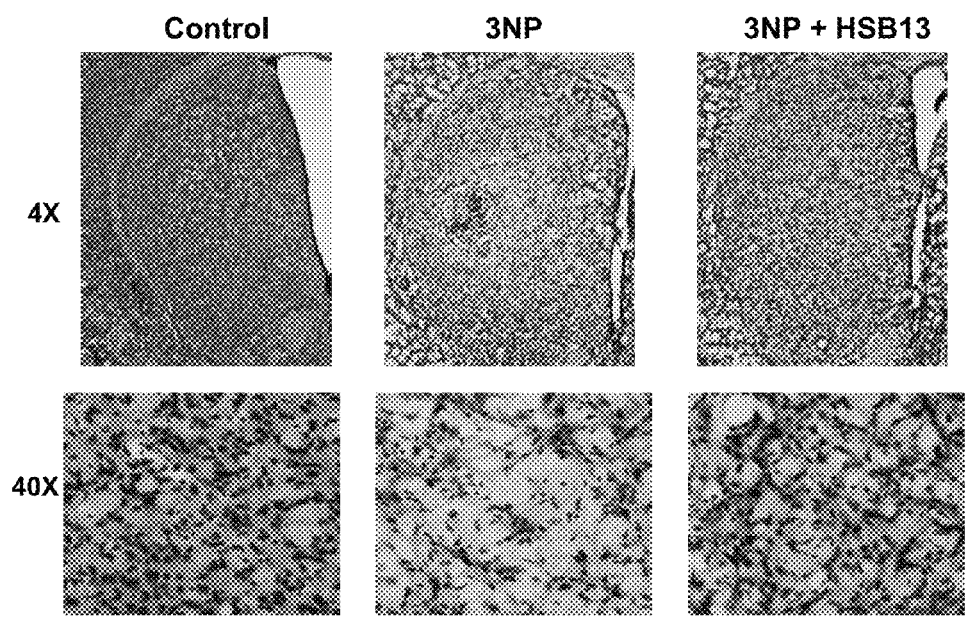
FIGS. 10A and 10B are images that shows that 3-NP is protective against 3-NP neurotoxicity in vivo.
Figure 10:
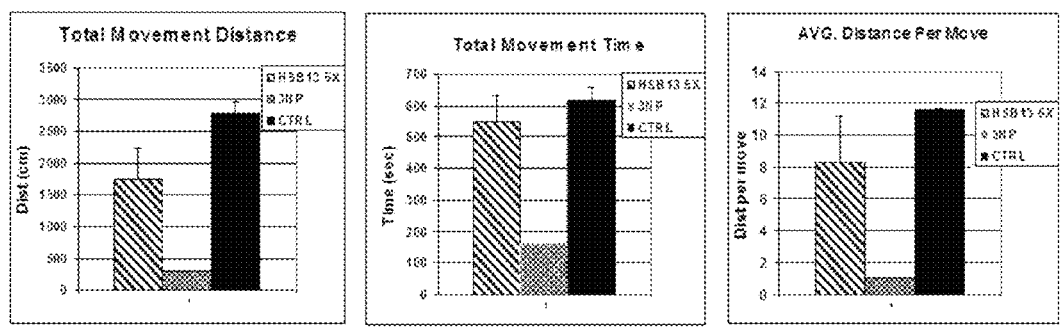

HSB-13 is neuroprotective in an in vivo model of Huntington's disease (HD). Nitropropionic acid (3-NP) administration in rodents and nonhuman primates replicates most of the clinical and pathophysiological hallmarks of HD including selective striatal degeneration, spontaneous choreiform and dystonic movements. Administration of this neurotoxin has thus served as a useful model for HD (reviewed in Brouillet et al., 1999). The efficacy of HSB-13 was determined. As shown in FIG. 10A, mice administered with 3-NP display extensive bilateral striatal lesions. This degeneration is substantially reduced by HSB-13 when administered at a concentration of 2.5 mg/kg body weight (FIG. 10). The protection by HSB-13 against 3-NP-induced striatal neurodegeneration correlated with a robust improvement of locomotor performance. Specifically, total movement episodes, total movement distance and mean velocity of movement, which were all impaired by 3-NP administration, were markedly higher in animals receiving HSB-13 (FIG. 10B).

3-Nitropropionic acid administration and behavioral evaluation. 8-week old C57BL/6 male mice (Charles River Laboratories, Inc, Wilmington, Mass.) were administered with 3-NP in ten intraperitoneal injections (50 mg/kg twice a day for 5 days) with or without HSB-13 92.5 mg/kg). Injections of HSB-13 were performed ~30 min before 3-NP administration. Control animals received saline injections. On the day following the 5 days of injection, locomotor activity was assessed using THE TRU-SCAN® activity monitoring system (Coulborn Instruments, PA) as previously described (Chin et al. 2004). The following behavioral parameters were selected: (i) Total movements episodes: each movement in the floor plane is a series of coordinate changes with no rest for at least 1 sample interval, (2) Total movement distance: the sum of all vectored X-Y coordinate changes in the floor plane, and (3) Mean velocity: the mean velocity of all X-T coordinate change defined movements. Following behavioral evaluation, the mice were deeply anesthetized and brains removed. The brains were fixed in 4% paraformaldehyde in 0.1 M phosphate buffer and cryoprotected in 20% sucrose in 0.1 M phosphate buffer. Coronal sections were cut on a cryostat at 50 microns and stained with cresyl violet (Sigma).

The present invention is the first demonstration of 1,4 benzoxazines as neuroprotective agents and raise the exciting possibility that this class of compounds represent a novel therapeutic agent for the treatment of human neurodegenerative disorders.

Evaluation of the effect of chemical compounds on cellular c-Raf and/or B-Raf activity. The activity of c-Raf or B-Raf are evaluated following their immunoprecipitation from cell lysates. Briefly, about 250 µg of protein is incubated with 1.0 µg of primary antibody (against either c-Raf or B-Raf) and 12 µl of Protein A/G PLUS-Agarose beads overnight. Immunoprecipitates are collected by centrifugation at 6000 rpm for 30 sec and washed twice with lysis buffer, twice with lysis buffer supplemented with 350 mM NaCl, and twice with kinase buffer (25 mM HEPES pH 7.4 and 10 mM $MgCl_2$). Purified recombinant GST-MEK1 K97M protein is added as a substrate in kinase buffer supplemented with 85 µm ATP for 35 minutes at 30° C. For in vitro kinase assays, the compounds are added in kinase buffer and incubated for 5 minutes at 30° C. prior starting the kinase reaction by ATP addition. The kinase reactions are stopped by addition of 6×SDS sample buffer and boiled for 5 minutes. Proteins are resolved by SDS-PAGE and subjected to Western blotting. The level of kinase activity is detected by a phospho-MEK antibody following Western blotting.

Effect of chemical compounds c-Raf and B-Raf purified from insect cells. In vitro kinase assays were performed using purified kinase (expressed by baculovirus in Sf9 insect cells) and synthetic substrates under standard conditions using the Kinase Profiling service of Upstate Biotechnology. Briefly, for each assay 5-10 mU of purified kinase is incubated with the chemical compound (0.1-1 uM concentration) in a buffer containing 8 mM MOPS, pH 7.2, 0.2 mM EDTA, 10 mM Mg Acetate and [$\gamma$-$^{33}$P-ATP] for 40 min at room temperature. MBP is used as substrate. Kinase activity is quantified by measuring $^{33}$P incorporation by spotting an aliquot on P30 filters, washing in 50 mM phosphoric acid and scintillation counting.

In some cases, effects on c-Raf and B-Raf are assayed by SignalChem as follows. Protein kinase assays (in duplicate or triplicate) were performed at ambient temperature for 20-40 minutes in a final volume of 25 µl. The assay was initiated by the addition of $^{33}$P-ATP and the reaction mixture incubated at ambient temperature for 20-40 minutes, depending on the protein kinase target. After the incubation period, the assay was terminated by spotting 10 µl of the reaction mixture onto Multiscreen phosphocellulose P81 plate. The Multiscreen phosphocellulose P81 plate was washed 3 times for approximately 15 minutes each in a 1% phosphoric acid solution.

The radioactivity on the P81 plate was counted in the presence of scintillation fluid in a Trilux scintillation counter. Blank control is included all the assay components except the addition of the appropriate substrate (replace with equal volume of assay dilution buffer), was set up for each protein kinase target. The corrected activity for each protein kinase target was determined by removing the blank control value.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Balderamos M, Ankati H, Akubathini S K, Patel A V, Kamila S, Mukherjee C, Wang L, Biehl E R, D'Mello S R. (2008) Synthesis and Structure-Activity Relationship Studies of 3-Substituted Indolin-2-ones as Effective Neuroprotective Agents. Exp Biol Med. 233:1395-1402.

Bhave S V, Hoffman P L. (2004) Phosphatidylinositol 3'-OH kinase and protein kinase A pathways mediate the anti-apoptotic effect of pituitary adenylyl cyclase-activating polypeptide in cultured cerebellar granule neurons: modulation by ethanol. J. Neurochem. 88:359-369.

Brand A H and Perrimon N, (1993) Targeted gene expression as a means of altering cell fates and generating dominant phenotypes. Development (Cambridge, England) 118: 401-415.

Boutillier, A. L., E. Trinh, and J. P. Loeffler (2002) Constitutive repression of E2F1 transcriptional activity through HDAC proteins is essential for neuronal survival. Ann. N.Y. Acad. Sci. 973:438-442.

Chen H M, Wang L, D'Mello S R. (2008a) Inhibition of ATF-3 expression by B-Raf mediates the neuroprotective action of GW5074. J. Neurochem. 2008 May; 105:1300-1312.

Chen H-C, Wang L, D'Mello S R. (2008b) A commercially available and commonly used chemical inhibitor of PKR protects neurons by inhibiting cyclin-dependent kinase Eur. J. Neurosci. (in press).

Chin P C, Liu L, Morrison B, Bottiglieri T, Ratan R R, D'Mello S R. (2004) The c-Raf inhibitor GW5074 provides neuroprotection in vitro and in an animal model of neurodegeneration through a MEK-ERK and Akt-independent mechanism. J. Neurochem. 90: 595-608.

D'Mello S R, Galli C, Calissano P. (1993) Induction of Apoptosis in Cerebellar Granule Neurons by Lowering of Extracellular Potassium: Inhibition of Death by IGF-I and cyclic AMP. Proc. Natl. Acad. Sci. (USA) 90: 10989-10993.

D'Mello S R, Chin P C. (2005) Treating neurodegenerative conditions through the understanding of neuronal apoptosis. Curr Drug Targets CNS Neurol Disord. 4:3-23.

Estus S., Zaks W. J., Freeman R. S., Gruda M., Bravo R. and Johnson E. M., Jr. (1994) Altered gene expression in neurons during programmed cell death: identification of c-jun as necessary for neuronal apoptosis. J Cell Biol 127, 1717-1727.

Fossgreen A, Bruckner B, Czech C, Masters C L, Beyreuther K, et al., (1998) Transgenic *Drosophila* expressing human amyloid precursor protein show gamma-secretase activity and a blistered-wing phenotype. Proc Natl Acad Sci USA 95: 13703-13708.

Greeve I, Kretzschmar D, Tschape J A, Beyn A, Brellinger C, et al., (2004) Age-dependent neurodegeneration and Alzheimer-amyloid plaque formation in transgenic *Drosophila*. J Neurosci 24: 3899-3906.

Hai T., Wolfgang C. D., Marsee D. K., Allen A. E. and Sivaprasad U. (1999) ATF3 and stress responses. Gene Expr 7, 321-335.

Ham J., Babij C., Whitfield J., Pfarr C. M., Lallemand D., Yaniv M. and Rubin L. L. (1995) A c-Jun dominant negative mutant protects sympathetic neurons against programmed cell death. Neuron 14, 927-939.

Hanson, M G, Jr; Shen, S; Wiemelt, A P; McMorris, F A; Barres, B A. (1998) Cyclic AMP elevation is sufficient to promote the survival of spinal motor neurons in vitro. J. Neurosci. 18:7361-7371.

Hetman M, Kharebava G. (2006) Survival signaling pathways activated by NMDA receptors. Curr Top Med. Chem. 6:787-799.

Johnson K, Liu L, Majdzadeh N, Chavez C, Chin P C, Morrison B, Wang L, Park J, Chugh P, Chen H M, D'Mello S R. (2005) Inhibition of neuronal apoptosis by the cyclin-dependent kinase inhibitor GW8510: identification of 3' substituted indolones as a scaffold for the development of neuroprotective drugs. J. Neurochem. 93:538-548.

Kingsbury A E, Gallo V, Woodhams P L, Balazs R. (1985) Survival, morphology and adhesion properties of cerebellar interneurones cultured in chemically defined and serum-supplemented medium. Brain Res. 349:17-25.

Levi, G., Aloisi, F., Ciotti, M. T., Thangnipon, W., Kingsburry, A. and Balazs, R., Preparation of 98% pure cerebellar granule cell cultures (1989) In A. Shahar, J. Vellis and B. A. Habu (Eds.), Dissection and Tissue Culture Manual of the Nervous system, Alan R. Liss, New York, pp. 211-214.

Li M, Wang X, Meintzer M K, Laessig T, Birnbaum M J, Heidenreich K A. (2000) Cyclic AMP promotes neuronal survival by phosphorylation of glycogen synthase kinase 3beta. Mol Cell Biol. 20:9356-9363.

Linseman D A, Bartley C M, Le S S, Laessig T A, Bouchard R J, Meintzer M K, Li M, Heidenreich K A. (2003) Inactivation of the myocyte enhancer factor-2 repressor histone deacetylase-5 by endogenous $Ca(2+)$//calmodulin-dependent kinase II promotes depolarization-mediated cerebellar granule neuron survival. J Biol. Chem. 278:41472-41481.

Majdzadeh N, Wang L, Morrison B E, Bassel-Duby R, Olson E N, D'Mello S R. (2008) HDAC4 inhibits cell-cycle progression and protects neurons from cell death. Dev Neurobiol. 68:1076-1092.

Morozova N, Khrapko K, Panee J, Liu W, Harney J W, et al. (2007) Glutathione depletion in hippocampal cells increases levels of H and L ferritin and glutathione S-transferase mRNAs. Genes Cells 12: 561-567.

Morrison B E, Majdzadeh N, Zhang X, Lyles L, Bassel-Duby R, Olson E N, D'Mello S R (2006) Neuroprotection by histone deacetylase-related protein. Mol. Cell. Biol. 26: 3550-3564.

Murphy, T. H., Schnaar, R. L. & Coyle, J. T. (1990) Immature cortical neurons are uniquely sensitive to glutamate toxicity by inhibition of cystine uptake. Faseb J, 4, 1624-1633.

Ratan, R. R., Murphy, T. H. & Baraban, J. M. (1994a) Macromolecular synthesis inhibitors prevent oxidative stress-induced apoptosis in embryonic cortical neurons by shunting cysteine from protein synthesis to glutathione. J Neurosci, 14, 4385-4392.

Ratan, R. R., Murphy, T. H., & Baraban, J. M. (1994b) Oxidative stress induces apoptosis in embryonic cortical neurons. J Neurochem, 62, 376-379.

Rydel, R E; Greene, L A. cAMP analogs promote survival and neurite outgrowth in cultures of rat sympathetic and sensory neurons independently of nerve growth factor. Proc Natl Acad Sci USA. 1988; 85:1257-1261.

Salminen A, Tapiola T, Korhonen P, Suuronen T. (1998) Neuronal apoptosis induced by histone deacetylase inhibitors. Brain Res Mol Brain Res. 61:203-206.

Schenkel J. (2004) Activation of the c-Jun transcription factor following neurodegeneration in vivo. Neurosci Lett. 361:36-39.

See V, Boutillier A L, Bito H, Loeffler J P. (2001) Calcium/calmodulin-dependent protein kinase type IV (CaMKIV)

inhibits apoptosis induced by potassium deprivation in cerebellar granule neurons. FASEB J. 15:134-144.

Thangnipon W, Kingsbury A, Webb M, Balazs R. (1983) Observations on rat cerebellar cells in vitro: influence of substratum, potassium concentration and relationship between neurones and astrocytes. Brain Res. 313:177-89.

Vlug A. S., Teuling E., Haasdijk E. D., French P., Hoogenraad C. C. and Jaarsma D. (2005) ATF3 expression precedes death of spinal motoneurons in amyotrophic lateral sclerosis-SOD1 transgenic mice and correlates with c-Jun phosphorylation, CHOP expression, somato-dendritic ubiquitination and Golgi fragmentation. Eur J Neurosci 22, 1881-1894.

Watson A., Eilers A., Lallemand D., Kyriakis J., Rubin L. L. and Ham J. (1998) Phosphorylation of c-Jun is necessary for apoptosis induced by survival signal withdrawal in cerebellar granule neurons. *J Neurosci* 18, 751-762.

Yalcin A, Koulich E, Mohamed S, Liu L, D'Mello S R (2003) Apoptosis in cerebellar granule neurons is associated with CBP hyperphosphorylation and reduced interaction between CBP and NF-κB J. Neurochem. 84: 397-408.

The invention claimed is:

1. A pharmaceutical compound for reducing neuronal cell death in a subject comprising:
   an effective amount of a composition of formula (I) disposed in a pharmaceutical carrier, wherein the effective amount is sufficient to reduce neuronal cell death in a subject:

wherein Ar is a phenyl substituted with one or more bromides, chlorides, hydroxyls or acetoxy groups;
   X is O; R is a H; and G is an amine containing group.

2. The compound of claim 1, wherein Ar is 3,5-dibromo-4-hydoxyphenyl.

3. The compound of claim 1, wherein G is a $NH_2$.

4. The compound of claim 1, wherein Ar is 3, 5, dibromo-4-acetoxyphenyl and G is a $NH_2$.

5. A method of reducing neuronal cell death in a subject in need thereof, comprising:
   administering a composition comprising a compound according to claim 4 in an amount effective to reduce neurodegeneration.

6. The method according to claim 5, wherein Ar is 3,5-dibromo-4-hydoxyphenyl.

7. The method according to claim 5, wherein G is a $NH_2$ group.

8. The method according to claim 5, wherein the neuronal cell death is associated with one or more of Alzheimer's disease, Parkinson's disease, Huntington's disease, Amyotropic lateral sclerosis, traumatic brain injury, a stroke, and an ischemic stroke.

9. A method of reducing activity of a kinase in a subject in need thereof, comprising:
   administering a composition comprising a compound according to claim 1 in an amount effective to reduce activity of a kinase.

10. The method of claim 9, further comprising measuring kinase activity level in the subject.

11. The method of claim 9, wherein the kinase is selected from the group consisting of GSK3α, GSK3β, p38β, and B-Raf.

12. The method of claim 9, wherein the kinase is selected from the group consisting of CDK1, CDK2, ROCK1, JNK2, MLK3, and c-Raf.

13. A composition having the structure

14. A method of reducing neuronal cell death in a subject in need thereof, comprising:
   administering an amount effective of a composition to reduce neurodegeneration wherein the a composition having the structure 15. The method according to claim 14, wherein the neuronal cell death is associated with one or more of Alzheimer's disease, Parkinson's disease, Huntington's disease, Amyotropic lateral sclerosis, traumatic brain injury, a stroke, and an ischemic stroke.

16. A method of reducing activity of a kinase in a subject in need thereof, comprising:
   administering an amount effective of a composition to reduce activity of a kinase wherein the composition having the structure 17. The method of claim 16, further comprising measuring kinase activity level in the subject.

18. The method of claim 16, wherein the kinase is selected from the group consisting of GSK3α, GSK3β, p38β, and B-Raf.

19. The method of claim 16, wherein the kinase is selected from the group consisting of CDK1, CDK2, ROCK1, JNK2, MLK3, and c-Raf.

* * * * *